United States Patent [19]

Lennon et al.

[11] Patent Number: 5,721,361

[45] Date of Patent: Feb. 24, 1998

[54] PROCESS FOR PREPARING SUBSTITUTED POLYAZAMACROCYCLES

[75] Inventors: Patrick J. Lennon, Clayton; Susan L. Henke, Webster Grove; Karl W. Aston, Pacific, all of Mo.

[73] Assignee: The Monsanto Company, St. Louis, Mo.

[21] Appl. No.: 665,070

[22] Filed: Jun. 11, 1996

Related U.S. Application Data

[63] Continuation of Ser. No. 486,434, Jun. 7, 1995, abandoned.

[51] Int. Cl.$^6$ .................................................. C07D 225/02
[52] U.S. Cl. ............................ 540/450; 540/451; 540/452
[58] Field of Search ................................. 540/450, 451, 540/452

[56] References Cited

U.S. PATENT DOCUMENTS

| | | | |
|---|---|---|---|
| 4,569,750 | 2/1986 | Brownswell et al. | 208/48 AA |
| 4,923,985 | 5/1990 | Gansow et al. | 540/474 |
| 5,126,464 | 6/1992 | Burrows et al. | 549/520 |
| 5,298,618 | 3/1994 | Speranza et al. | 540/454 |
| 5,322,681 | 6/1994 | Klaveness | 424/9 |
| 5,324,334 | 6/1994 | Brois et al. | 44/336 |
| 5,386,028 | 1/1995 | Tilstam et al. | 540/474 |

FOREIGN PATENT DOCUMENTS

| | | | |
|---|---|---|---|
| 0 524 161 A1 | 1/1993 | European Pat. Off. | C07F 13/00 |
| WO A 92/08707 | 5/1992 | WIPO | C07D 259/00 |
| WO 93/25243 | 12/1993 | WIPO | A61K 49/00 |
| WO A 94/15925 | 7/1994 | WIPO . | |
| WO A 95/28968 | 11/1995 | WIPO | A61K 49/00 |

OTHER PUBLICATIONS

Dariez et al., Tetra Letters., vol. 48, No. 21, pp. 4347–4358, 1992.
Fieser & Fieser., Reapents for Org. Synthesis p. 1313, 1967.
Shakir et al., Tetrahedron., vol. 56, pp. 3339–3344, 1991.
Jean–Paul Behr et al. Macrotricyclic and Macropentacyclic Ditopic Receptor Molecules, Synthesis, Crystal Structure and Substrate Binding, *Tetrahedron Letters*, vol. 28, No. 18, pp. 1989–1992, (1987).
Marie–Christine Duriez et al. Macrocylic Polyether Tetralactams I: Synthesis and Cyclization Studies, *Tetrahedron*, vol. 48, No. 21, pp. 4347–4358 (1992).
Louis F. Fieser et al. Reagents for Organic Synthesis, *John Wiley and Sons, Inc.* (1967).
Krzysztof E. Krakowiak et al. Synthesis of Aza–Crown Ethers, *Chemical Reviews*, vol. 89, No. 4, 929–972 (1989).
McMurry et al. Convenient Synthesis of Bifunctional Tetraaza Macrocycles, *Bioconjugate Chem*, vol. 3, No. 2, pp. 108–117, (1992).
Moberg et al. Synthesis and Structure of Macrocyclic Amides Containing a 2,2'–Dipyridylmethane Unit. A New Class of Chiral Macrocyclic Ligands, *J. Org. Chem.*, vol. 56, pp. 3339–3344, (1991).
Mohammad Shakir et al. Divalent Cobalt, Nickel, Copper and Zinc Complexes of Tetraaza Macrocycles Bearing Polyamide Groups: Synthesis and Characterization, *Tetrahedron*, vol. 12, No. 23, pp. 2775–2780 (1993).

*Primary Examiner*—Mukund J. Shah
*Assistant Examiner*—Pavanaram K. Sripada
*Attorney, Agent, or Firm*—Michael J. Roth; Roger A. Williams

[57] ABSTRACT

A process for preparing a substituted polyazamacrocycle is provided which comprises contacting a diamine or triamine and a dicarboxylic acid or ester or anhydride thereof in the presence of a suitable base and a suitable solvent to produce the substituted polyazamacrocycle provided that when an ester of said dicarboxylic acid is used, said suitable base is optional, and when said dicarboxylic acid or an anhydride of said dicarboxylic acid is used, the reaction mixture further comprises a suitable coupling agent.

24 Claims, No Drawings

PROCESS FOR PREPARING SUBSTITUTED POLYAZAMACROCYCLES

This is a continuation of application Ser. No. 08/486,434 filed Jun. 7, 1995 now abandoned.

BACKGROUND OF THE INVENTION

This invention relates to a process for preparing substituted polyazamacrocycles. In one aspect, this invention relates to a process for preparing substituted fifteen-membered and sixteen-membered pentaazamacrocyclic ligands which are useful in the sequestration of transition metal ions. In a further aspect, this invention relates to a process for preparing manganese(II) or manganese(III) complexes of substituted fifteen-membered and sixteen-membered pentaazamacrocyclic ligands which catalytically dismutate superoxide.

The substituted polyazamacrocycles of the invention, which are useful in the sequestration of transition metal ions, can be used in qualitative or quantitative assays of transition metal ions. The substituted polyazamacrocycles of the invention are also useful as intermediates in the preparation of manganese complexes of substituted fifteen-membered and sixteen-membered pentaazamacrocyclic ligands. The manganese complexes of substituted fifteen-membered and sixteen-membered pentaazamacrocyclic ligands are low molecular weight mimics of superoxide dismutase (SOD) which are useful as therapeutic agents for inflammatory disease states or disorders which are mediated, at least in part, by superoxide. The manganese (II) complexes of substituted fifteen-membered pentaazamacrocyclic ligands are also useful as magnetic resonance imaging (MRI) contrast agents.

The enzyme superoxide dismutase catalyzes the conversion of superoxide into oxygen and hydrogen peroxide according to equation (1) (hereinafter referred to as dismutation). Reactive oxygen/metabolites derived from superoxide are postulated to contribute to the tissue pathology in a number of

$$O_2^- - O_2^- + 2H^+ \rightarrow O_2 + H_2O_2 \quad (1)$$

inflammatory diseases and disorders, such as reperfusion injury to the ischemic myocardium, inflammatory bowel disease, rheumatoid arthritis, osteoarthritis, atherosclerosis, hypertension, metastasis, psoriasis, organ transplant rejections, radiation-induced injury, asthma, influenza, stroke, burns and trauma. See, for example, Bulkley, G. B., Reactive oxygen metabolites and reperfusion injury: aberrant triggering of reticuloendothelial function, The Lancet, Vol. 344, pp. 934–36, Oct. 1, 1994; Grisham, M. B., Oxidants and free radicals in inflammatory bowel disease, The Lancet, Vol. 344, pp. 859–861, Sep. 24, 1994; Cross, C. E. et al., Reactive oxygen species and the lung, The Lancet, Vol. 344, pp. 930–33, Oct. 1, 1994; Jenner, P., Oxidative damage in neurodegenerative disease, The Lancet, Vol. 344, pp. 796–798, Sep. 17, 1994; Cerutti, P. A., Oxy-radicals and cancer, The Lancet, Vol. 344, pp. 862–863, Sep. 24, 1994 Simic, M. G., et al, Oxygen Radicals in Biology and Medicine, Basic Life Sciences, Vol. 49, Plenum Press, New York and London, 1988; Weiss J. Cell. Biochem., 1991 Suppl. 15C, 216 Abstract C110 (1991); Petkau, A., Cancer Treat. Rev. 13, 17 (1986); McCord, J. Free Radicals Biol. Med., 2, 307 (1986); and Bannister, J. V. et at, Cdt. Rev. Biochem., 22, 111 (1987). The above-identified references from The Lancet teach the nexus between free radicals derived from superoxide and a variety of diseases. In particular, the Bulkley and Grisham references Specifically teach that there is a nexus between the dismutation of superoxide and the final disease treatment.

It is also known that superoxide is involved in the breakdown of endothelium-derived vascular relaxing factor (EDRF), which has been identified as nitric oxide (NO), and that EDRF is protected from breakdown by superoxide dismutase. This suggests a central role for activated oxygen species derived from superoxide in the pathogenesis of vasospasm, thrombosis and atherosclerosis. See, for example, Gryglewski, R. J. et at., "Superoxide Anion is Involved in the Breakdown of Endothelium-derived Vascular Relaxing Factor", Nature, Vol. 320, pp. 454–56 (1986) and Palmer, R. M. J. et at., "Nitric Oxide Release Accounts for the Biological Activity of Endothelium Derived Relaxing Factor", Nature, Vol. 327, pp. 523–26 (1987).

Clinical trials and animal studies with natural, recombinant and modified superoxide dismutase enzymes have been completed or are ongoing to demonstrate the therapeutic efficacy of reducing superoxide levels in the disease states noted above. However, numerous problems have arisen with the use of the enzymes as potential therapeutic agents, including lack of oral activity, short half-lives in vivo, immunogenicity with nonhuman derived enzymes, and poor tissue distribution.

SUMMARY OF THE INVENTION

It is an object of the invention to provide a process for preparing substituted fifteen-membered and sixteen-membered pentaazamacrocyclic ligands. It is a further object of the invention to provide a process for preparing reduced substituted fifteen-membered and sixteen-membered pentaazamacrocyclic ligands. It is yet a further object of the invention to provide a process for preparing manganese(II) or manganese(II) complexes of substituted fifteen-membered and sixteen-membered pentaazamacrocyclic ligands.

According to the invention, a process for preparing a substituted polyazamacrocycle is provided which comprises contacting a dime and a dicarboxylic acid or ester or anhydride thereof in the presence of a suitable base and a suitable solvent under reaction conditions sufficient to produce the substituted polyazamacrocycle, provided that when an ester of said dicarboxylic acid is used, said suitable base is optional and when said dicarboxylic acid or an anhydride of said dicarboxylic acid is used, the reaction mixture further comprises a suitable coupling agent. In one embodiment of the invention, the substituted polyazamacrocycle prepared according to the invention is reduced to produce a reduced substituted polyazamacrocycle. In a further embodiment of the invention, a manganese complex of the reduced substituted polyazamacrocycle is produced by reacting the reduced substituted polyazamacrocycle with a manganese compound under essentially anhydrous and anaerobic conditions and, optionally, further conducting an exchange reaction with the manganese complex to exchange the axial ligands on the manganese complex.

Further according to the invention, a process for preparing a substituted polyazamacrocycle is provided which comprises contacting a triamine and a dicarboxylic acid or ester or anhydride thereof in the presence of a suitable base and a suitable solvent under conditions of time and temperature sufficient to produce the substituted polyazamacrocycle, provided that when an ester of said dicarboxylic acid is used, said suitable base is optional and when said dicarboxylic acid or an anhydride of said dicarboxylic acid is used, the reaction mixture further comprises a suitable coupling agent.

In one embodiment of the invention, the substituted polyazamacrocycle prepared according to the invention is reduced to produce a reduced substituted polyazamacrocycle. In a further embodiment of the invention, a manganese complex of the reduced substituted polyazamacrocycle is produced by reacting the reduced substituted polyazamacrocycle with a manganese compound under essentially anhydrous and anaerobic conditions and, optionally, further conducting an exchange reaction with the manganese complex to exchange the axial ligands on the manganese complex.

DETAILED DESCRIPTION OF THE INVENTION

One aspect of this invention relates to a process for preparing a substituted polyazamacrocycle comprising contacting (a) a diamine represented by the formula:

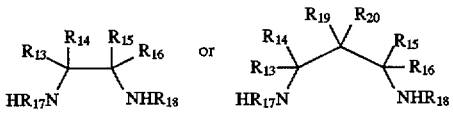

and (b) a dicarboxylic acid or ester thereof represented by the formula:

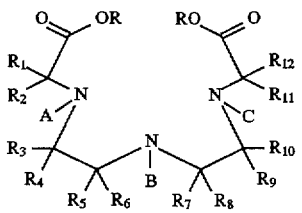

or an anhydride thereof; in the presence of a suitable base and a suitable solvent under reaction conditions sufficient to produce the substituted polyazamacrocycle represented by the formula:

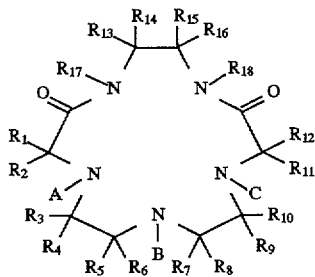

or

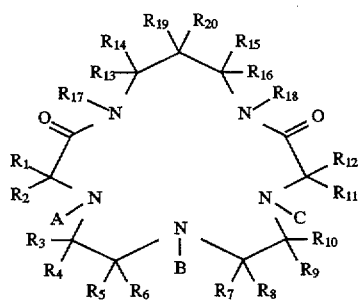

provided that when an ester of said dicarboxylic acid is used, said suitable base is optional and when said dicarboxylic acid or an anhydride of said dicarboxylic acid is used, the reaction mixture further comprises a suitable coupling agent; wherein $R_1$, $R_2$, $R_3$, $R_4$, $R_5$, $R_6$, $R_7$, $R_8$, $R_9$, $R_{10}$, $R_{11}$ and $R_{12}$ are independently selected from hydrogen or alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals or radicals attached to the α-carbon of α-amino acids; or $R_3$ or $P_4$ and $R_5$ or $R_6$, and $R_7$ or $R_8$ and $R_9$ or $R_{10}$ together with the carbon atoms to which they are attached independently form a saturated, partially saturated or unsaturated cyclic having 3 to 20 carbon atoms; or $R_1$ or $R_2$ and $R_3$ or $R_4$, $R_5$ or $R_6$ and $R_7$ or $R_8$, and $R_9$ or $R_{10}$ and $R_{11}$ or $R_{12}$ together with the carbon atoms to which they are attached independently form a nitrogen containing heterocycle having 2 to 20 carbon atoms provided that when the nitrogen containing heterocycle is an aromatic heterocycle which does not contain a substituent attached to the nitrogen, the hydrogen attached to the nitrogen in the formula, which nitrogen is also in the macrocycle and the R groups attached to the same carbon atoms of the macrocycle are absent;

$R_1$ and $R_2$, $R_3$ and $R_4$, $R_5$ and $R_6$, $R_7$ and $R_8$, $R_9$ and $R_{10}$, and $R_{11}$ and $R_{12}$ together with the carbon atom to which they are attached independently form a saturated, partially saturated or unsaturated ring structure having 3 to 20 carbon atoms, or $R_1$ and $R_2$, $R_3$ and $R_4$, $R_5$ and $R_6$, $R_7$ and $R_8$, $R_9$ and $R_{10}$, and $R_{11}$ and $R_{12}$ independently are =O or =S; and combinations thereof; and wherein $R_{13}$, $R_{14}$, $R_{15}$, $R_{16}$, $R_{19}$ and $R_{20}$ are independently selected from hydrogen or alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals; or $R_{13}$ and $R_{14}$, $R_{15}$ and $R_{16}$, and $R_{19}$ and $R_{20}$ together with the carbon atom to which they are attached independently form a saturated, partially saturated or unsaturated ring structure having 3 to 20 carbon atoms; or $R_{19}$ and $R_{20}$ are independently $-OR_{23}$, $-OH$, $-SR_{23}$, $-NR_{23}R_{24}$, $-P(O)(OR_{25})(OR_{26})$ or $-P(O)(R_{25})(OR_{26})$; or $R_{19}$ and $R_{20}$ are =O, =S, =NR_{23}$, =N—OH, =N—OR_{23}$, =N—O—C(O)—$R_{23}$, or =CR_{23}R_{24}$; or $R_{13}$ or $R_{14}$ and $R_{15}$ or $R_{16}$ together with the carbon atoms to which they are attached 30 independently form a saturated, partially saturated or unsaturated cyclic having 3 to 20 carbon atoms, provided that if said diamine has three carbons between the nitrogen atoms, the saturated, partially saturated or unsaturated cyclic has 4 to 20 carbon atoms; or $R_{13}$ or $R_{14}$ and $R_{19}$ or $R_{20}$, or $R_{15}$ or $R_{16}$ and $R_{19}$ or R20 together with the carbon atoms to which they are attached independently form a saturated, partially saturated or unsaturated cyclic having 3 to 20 carbon atoms; and combinations thereof;

wherein $R_{17}$ and $R_{18}$ are independently selected from hydrogen and alkyl or aryl groups;

wherein R is hydrogen or alkyl or aryl groups;

wherein $R_{23}$ and $R_{24}$ are independently selected from alkyl, aralkyl or aryl groups;

$R_{25}$ and $R_{26}$ are independently selected from hydrogen, alkyl, aralkyl or aryl groups and wherein A, B and C are independently selected from hydrogen, alkyl, aryl, aralkyl, cycloalkyl, $-OR_{21}$, $-SO_2R_{21}$, $-COOR_{21}$, $-COR_{21}$, $-CONR_{21}R_{22}$, $R_{21}R_{22}P$ (O), $(R_{21}O)(R_{22}O)P(O)$, $R_{21}R_{22}P(S)$, $-SOR_{21}$ or $-Si(OR_{21})_3$, provided that when the two "R" groups on a carbon adjacent to the nitrogen are =O or =S, A, B and C are hydrogen, alkyl, aralkyl or aryl and $R_{21}$ and $R_{22}$ are independently selected from hydrogen, alkyl, aryl, aralkyl or alkaryl groups.

As used herein, the term "anhydride" means an intramolecular anhydride of the dicarboxylic acid or intermolecular anhydrides of the dicarboxylic acid of linear or cyclic form.

For producing a reduced substituted polyazamacrocycle, the process of the invention further comprises reducing the substituted polyazamacrocycle prepared according to the process of the invention to produce a reduced substituted polyazamacrocycle of the formula:

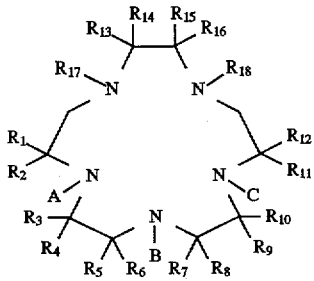

or

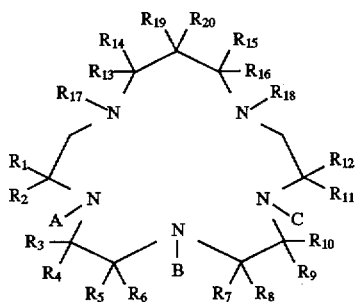

wherein A, B and C are independently selected from hydrogen, alkyl, aryl, aralkyl and cycloalkyl groups, and any "R" groups attached to the same carbon atom of the macrocycle which were =O or =S will be reduced to —OH or —SH.

The reduction of the substituted polyazamacrocycle is conducted in the presence of any suitable reducing agent under conventional reduction conditions known to those skilled in the arc The currently preferred reducing agents are selected from the group consisting of aluminum hydrides and boron hydrides. In particular, the preferred reducing agents are selected from the group consisting of lithium aluminum hydride, borane and sodium bis(2-methoxyethoxy) aluminum hydride.

For producing a manganese complex of the reduced substituted polyazamacrocycle, the process of the invention further comprises reacting the reduced substituted polyazamacrocycle with a manganese compound under essentially anhydrous and anaerobic conditions to produce a manganese complex represented by the formula:

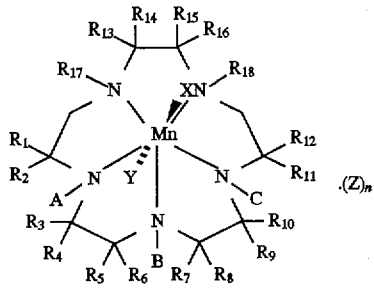

or

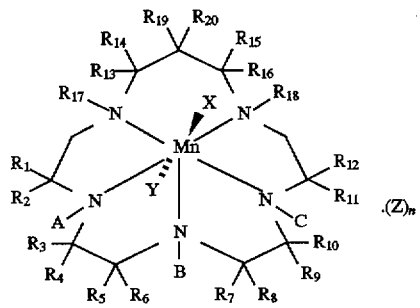

and, optionally, further conducting an exchange reaction with the manganese complex to exchange the ligands X, Y and Z on the manganese complex.

When the diamine is represented by the formula:

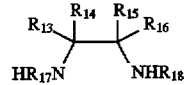

it is currently preferred that $R_{13}$, $R_{14}$, $R_{15}$ and $R_{16}$ are independently selected from hydrogen or alkyl; or $R_{13}$ or $R_{14}$ and $R_{15}$ or $R_{16}$ together with the carbon atoms to which they are attached independently form a saturated, partially saturated or unsaturated cyclic having 3 to 20 carbon atoms. In one preferred embodiment, at least one of $R_{13}$, $R_{14}$, $R_{15}$ and $R_{16}$ is an alkyl group. More preferably, at least one of $R_{13}$ and $R_{14}$ and at least one of R15 and $R_{16}$ is an alkyl group. In another preferred embodiment, $R_{13}$ and $R_{16}$ together with the carbon atoms to which they are attached independently form a sainted, partially saturated or unsaturated cyclic having 3 to 20 carbon atoms and $R_{14}$ and $R_{15}$ are hydrogen.

When the diamine is represented by the formula:

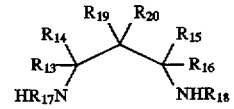

it is currently preferred that $R_{13}$, $R_{14}$, $R_{15}$, $R_{16}$, $R_{19}$ and $R_{20}$ are independently selected from hydrogen or alkyl; or $R_{13}$ or $R_{14}$ and $R_{19}$ or $R_{20}$; or $R_{15}$ or $R_{16}$ and $R_{19}$ or $R_{20}$ together with the carbon atoms to which they are attached independently form a saturated, partially saturated or unsaturated cyclic having 3 to 20 carbon atoms; or $R_{19}$ and $R_{20}$ together are =O or =S. In a preferred embodiment, at least one of $R_{13}$ or $R_{14}$ and $R_{19}$ or $R_{20}$, or $R_{15}$ or $R_{16}$ and $R_{19}$ or $R_{20}$ together with the carbon atoms to which they are attached independently form a saturated, partially saturated or unsaturated cyclic having 3 to 20 carbon atoms and the remaining "R" groups of the diamine are independently selected from hydrogen or alkyl, preferably hydrogen.

The currently preferred "R" groups of the dicarboxylic acids or esters thereof of the formula:

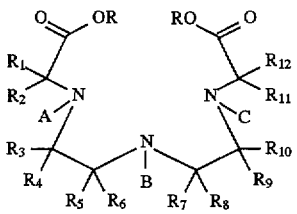

or anhydrides thereof; are as follows. It is currently preferred that $R_1$, $R_2$, $R_3$, $R_4$, $R_5$, $R_6$, $R_7$, $R_8$, $R_9$, $R_{10}$, $R_{11}$ and $R_{12}$ are independently selected from hydrogen, alkyl radicals or radicals attached to the α-carbon of α-amino acids; or $R_3$ or $R_4$ and $R_5$ or $R_6$, and $R_7$ or $R_8$ and $R_9$ or $R_{10}$ together with the carbon atoms to which they are attached independently form a saturated, partially saturated or unsaturated cyclic having 3 to 20 carbon atoms; or $R_1$ and $R_2$, $R_3$ and $R_4$, $R_5$ and $R_6$, $R_7$ and $R_8$, $R_9$ and $R_{10}$, and $R_{11}$ and $R_{12}$ independently are =O or =S. When $R_1$ and $R_2$, $R_3$ and $R_4$, $R_5$ and $R_6$, $R_7$ and $R_8$, $R_9$ and $R_{10}$, and $R_{11}$ and $R_{12}$ independently are =O or =S, it is preferred that each nitrogen atom have no more than one adjacent carbon atom which is substituted with =O or =S. In one preferred embodiment, at least one of $R_3$ or $R_4$ and $R_5$ or $R_6$, and $R_7$ or $R_8$ and $R_9$ or $R_{10}$ together with the carbon atoms to which they are attached independently form a saturated, partially saturated or unsaturated cyclic having 3 to 20 carbon atoms, and the remaining of $R_1$, $R_2$, $R_3$, $R_4$, $R_5$, $R_6$, $R_7$, $R_8$, $R_9$, $R_{10}$, $R_{11}$ and $R_{12}$ are independently selected from hydrogen, alkyl radicals or radicals attached to the α-carbon of α-amino acids. In another preferred embodiment, at least one, and more preferably at least two, of $R_1$, $R_2$, $R_3$, $R_4$, $R_5$, $R_6$, $R_7$, $R_8$, $R_9$, $R_{10}$, $R_{11}$ and $R_{12}$ are alkyl radicals or radicals attached to the α-carbon of α-amino acids, and the remaining of $R_1$, $R_2$, $R_3$, $R_4$, $R_5$, $R_6$, $R_7$, $R_8$, $R_9$, $R_{10}$, $R_{11}$ and $R_{12}$ are hydrogen.

In either diamine, it is currently preferred that $R_{17}$ and $R_{18}$ are hydrogen. In the dicarboxylic acid, it is currently preferred that R is hydrogen.

Another aspect of this invention relates to a process for preparing a substituted polyazamacrocycle comprising contacting (a) a triamine represented by the formula:

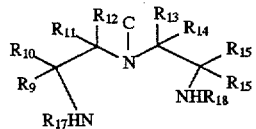

or

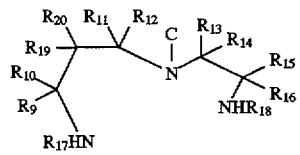

and (b) a dicarboxylic acid or ester thereof represented by the formula:

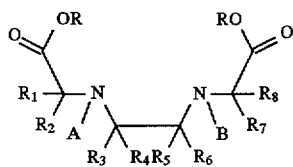

or an anhydride thereof; in the presence of a suitable base and a suitable solvent under reaction conditions sufficient to produce the substituted polyazamacrocycle represented by the formula:

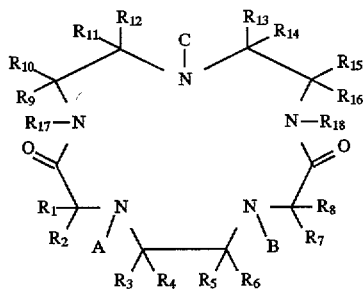

or

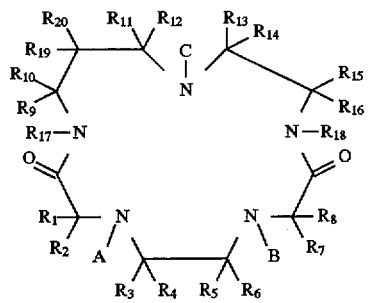

provided that when an ester of the dicarboxylic acid is used, the suitable base is optional and when the dicarboxylic acid or an anhydride of the dicarboxylic acid is used, the reaction mixture further comprises a suitable coupling agent; wherein $R_1$, $R_2$, $R_3$, $R_4$, $R_5$, $R_6$, $R_7$ and $R_8$ are independently selected from hydrogen or alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals or radicals attached to the α-carbon of α-amino acids; or $R_3$ or $R_4$ and $R_5$ or R6 together with the carbon atoms to which they are attached independently form a sainted, partially saturated or unsaturated cyclic having 3 to 20 carbon atoms; or $R_1$ or $R_2$ and $R_3$ or $R_4$, and $R_5$ or $R_6$ and $R_7$ or $R_8$ together with the carbon atoms to which they are attached independently form a nitrogen containing heterocycle having 2 to 20 carbon atoms provided that when the nitrogen containing heterocycle is an aromatic heterocycle which does not contain a substituent attached to the nitrogen, the hydrogen attached to the nitrogen in the formula, which nitrogen is also in the macrocycle and the R groups attached to the same carbon atoms of the macrocycle are absent; and combinations thereof;

$R_1$ and $R_2$, $R_3$ and $R_4$, $R_5$ and $R_6$, and $R_7$ and $R_8$ together with the carbon atom to which they are attached independently form a saturated, partially saturated or unsaturated ring structure having 3 to 20 carbon atoms or $R_1$ and $R_2$, $R_3$ and $R_4$, $R_5$ and $R_6$, and $R_7$ and $R_8$ independently are =O or =S; and combinations thereof; and wherein $R_9$, $R_{10}$, $R_{11}$, $R_{12}$, $R_{13}$, $R_{14}$, $R_{15}$, $R_{16}$, $R_{19}$ and $R_{20}$ are independently selected from hydrogen or alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals; or $R_9$ or $R_{10}$ and $R_{11}$ or $R_{12}$, and $R_{13}$ or $R_{14}$ and $R_{15}$ or $R_{16}$ together with the carbon atoms to which they are attached independently form a saturated, partially saturated or unsaturated cyclic having 3 to 20 carbon atoms, provided that if $R_9$ or $R_{10}$ and $R_{11}$ or $R_{12}$ together with the carbon atoms to which they are attached independently form a saturated, partially saturated or unsaturated cyclic and the diamine has three carbons between the nitrogen atoms, the saturated, partially saturated or unsaturated cyclic has 4 to 20 carbon atoms; or $R_9$ or $R_{10}$ and $R_{19}$ or $R_{20}$, or $R_{11}$ or $R_{12}$ and $R_{19}$ or $R_{20}$ together with the carbon atoms to which they are attached independently form a saturated, partially saturated or unsaturated cyclic having 3 to 20 carbon atoms; or $R_{11}$ or $R_{12}$ and $R_{13}$ or $R_{14}$ together with the carbon atoms to which they are attached independently form a nitrogen containing heterocycle having 2 to 20 carbon atoms provided that when the nitrogen containing heterocycle is an aromatic heterocycle which does not contain a substituent attached to the nitrogen, the hydrogen attached to the nitrogen in the formula, which nitrogen is also in the macrocycle and the R groups attached to the same carbon atoms of the macrocycle are absent;

$R_9$ and $R_{10}$, $R_{11}$ and $R_{12}$, $R_{13}$ and $R_{14}$, $R_{15}$ and $R_{16}$, and $R_{19}$ and $R_{20}$ together with the carbon atom to which they are attached independently form a saturated, partially saturated or unsaturated ring structure having 3 to 20 carbon atoms; or $R_{11}$ and $R_{12}$, and $R_{13}$ and $R_{14}$ independently are =O or =S; $R_{19}$ and $R_{20}$ independently are =O, =S, =NR$_{23}$, =N—OH, =N—OR$_{23}$, =N—O—C(O)—R$_{23}$, or =CR$_{23}$R$_{24}$; and combinations thereof;

wherein $R_{17}$ and $R_{18}$ are independently selected form hydrogen and alkyl groups;

wherein R is hydrogen or an alkyl group; and wherein A, B and C are independently selected from hydrogen, alkyl, aryl, aralkyl, cycloalkyl, —OR$_{21}$, —SO$_2$R$_{21}$, —COOR$_{21}$, —COR$_{21}$, —CONR$_{21}$R$_{22}$, R$_{21}$R$_{22}$P(O), (R$_{21}$O)(R$_{22}$O)P(O), R$_{21}$R$_{22}$P(S), —SOR$_{21}$ or —Si(OR$_{21}$)$_3$, provided that when the two "R" groups on a carbon adjacent to the nitrogen are =O or =S, A, B and C are hydrogen, alkyl, aralkyl or aryl, and R21 and R22 are independently selected from hydrogen, alkyl, aryl, aralkyl or alkaryl groups.

For producing a reduced substituted polyazamacrocycle, the process of the invention further comprises reducing the substituted polyazamacrocycle prepared according to the process of the invention to produce a reduced substituted polyazamacrocycle of the formula:

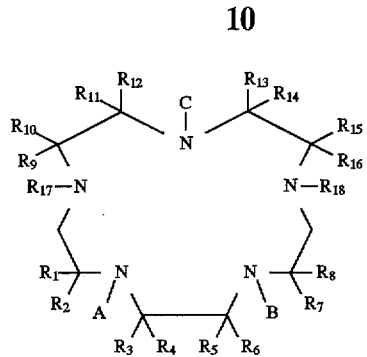

or

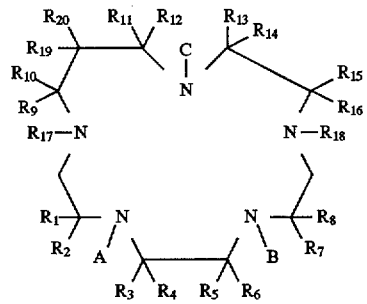

wherein A, B and C are independently selected from hydrogen, alkyl, aryl, aralkyl and cycloalkyl groups.

For producing a manganese complex of the reduced substituted polyazamacrocycle, the process of the invention further comprises reacting the reduced substituted polyazamacrocycle with a manganese compound under essentially anhydrous and anaerobic conditions to produce a manganese complex represented by the formula:

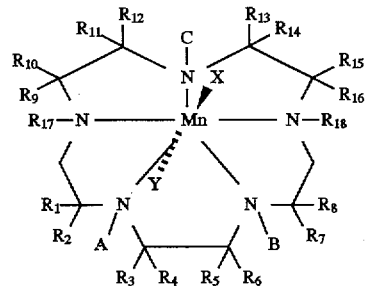

or

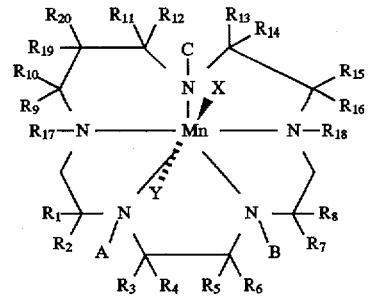

and, optionally, further conducting an exchange reaction with the manganese complex to exchange the ligands X, Y and Z on the manganese complex.

When the triamine is represented by the formula:

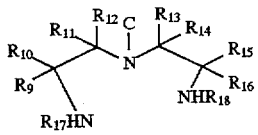

it is currently preferred that $R_9$, $R_{10}$, $R_{11}$, $R_{12}$, $R_{13}$, $R_{14}$, $R_{15}$ and $R_{16}$ are independently selected from hydrogen or alkyl; or $R_9$ or $R_{10}$ and $R_{11}$ or $R_{12}$, and $R_{13}$ or $R_{14}$ and $R_{15}$ or $R_{16}$ together with the carbon atoms to which they are attached independently form a sainted, partially saturated or unsaturated cyclic having 3 to 20 carbon atoms; or $R_{11}$ and $R_{12}$, and $R_{13}$ and $R_{14}$ independently are =O or =S. It is preferred that only one of $R_{11}$ and $R_{12}$, and $R_{13}$ and $R_{14}$ are =O or =S. In one preferred embodiment, at least one of $R_9$, $R_{10}$, $R_{11}$, $R_{12}$, $R_{13}$, $R_{14}$, $R_{15}$ and $R_{16}$ is an alkyl group. More preferably, at least one of $R_{13}$ and $R_{14}$ and at least one of $R_{15}$ and $R_{16}$ is an alkyl group or at least one of $R_9$ and $R_{10}$ and at least one of $R_{11}$ and $R_{12}$ is an alkyl group. In another preferred embodiment, $R_9$ and $R_{12}$ or $R_{13}$ and $R_{16}$ together with the carbon atoms to which they are attached independently form a saturated, partially saturated or unsaturated cyclic having 3 to 20 carbon atoms and the remaining R groups of the triamine are hydrogen.

When the triamine is represented by the formula:

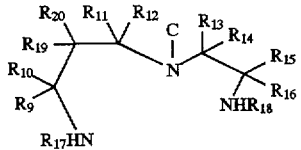

it is currently preferred that $R_9$, $R_{10}$, $R_{11}$, $R_{12}$, $R_{13}$, $R_{14}$, $R_{15}$, $R_{16}$, $R_{19}$ and $R_{20}$ are independently selected from hydrogen or alkyl; or $R_9$ or $R_{10}$ and $R_{19}$ or $R_{20}$, $R_{11}$ or $R_{12}$ and $R_{19}$ or $R_{20}$ or $R_{13}$ or $R_{14}$ and $R_{15}$ or $R_{16}$ together with the carbon atoms to which they are attached independently form a saturated, partially saturated or unsaturated cyclic having 3 to 20 carbon atoms; or $R_{11}$ and $R_{12}$, $R_{13}$ and $R_{14}$, and $R_{19}$ and $R_{20}$ independently are =O or =S. It is preferred that only one of $R_{11}$ and $R_{12}$, and $R_{13}$ and $R_{14}$ are =O or =S. In a preferred embodiment, at least one of $R_9$ or $R_{10}$ and $R_{19}$ or $R_{20}$, $R_{11}$ or $R_{12}$ and $R_{19}$ or $R_{20}$ or $R_{13}$ or $R_{14}$ and $R_{15}$ or $R_{16}$ together with the carbon atoms to which they are attached independently form a saturated, partially saturated or unsaturated cyclic having 3 to 20 carbon atoms and the remaining "R" groups of the triamine are independently selected from hydrogen or alkyl, preferably hydrogen.

The currently preferred "R" groups of the dicarboxylic acids or esters thereof of the formula:

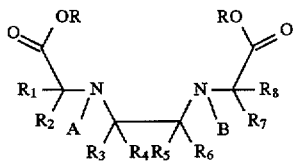

or anhydrides thereof are as follows. It is currently preferred that $R_1$, $R_2$, $R_3$, $R_4$, $R_5$, $R_6$, $R_7$ and $R_8$ are independently selected from hydrogen, alkyl radicals or radicals attached to the α-carbon of α-amino acids; or $R_3$ or $R_4$ and $R_5$ or $R_6$ together with the carbon atoms to which they are attached independently form a saturated, partially saturated or unsaturated cyclic having 3 to 20 carbon atoms; or $R_1$ and $R_2$, $R_3$ and $R_4$, $R_5$ and $R_6$, and $R_7$ and $R_8$ independently are =O or =S. When $R_1$ and $R_2$, $R_3$ and $R_4$, $R_5$ and $R_6$, and $R_7$ and $R_8$ independently are =O or =S, it is preferred that each nitrogen atom have no more than one adjacent carbon atom which is substituted with =O or =S. In one preferred embodiment, $R_3$ or $R_4$ and $R_5$ or $R_6$ together with the carbon atoms to which they are attached independently form a saturated, partially saturated or unsaturated cyclic having 3 to 20 carbon atoms, and the remaining of $R_1$, $R_2$, $R_3$, $R_4$, $R_5$, $R_6$, $R_7$ and $R_8$ are independently selected from hydrogen, alkyl radicals or radicals attached to the α-carbon of α-amino acids. In another preferred embodiment, at least one, and more preferably at least two, of $R_1$, $R_2$, $R_3$, $R_4$, $R_5$, $R_6$, $R_7$ and $R_8$ are alkyl radicals or radicals attached to the α-carbon of α-amino acids, and the remaining of $R_1$, $R_2$, $R_3$, $R_4$, $R_5$, $R_6$, $R_7$ and $R_8$ are hydrogen.

In either triamine, it is currently preferred that $R_{17}$ and $R_{18}$ are hydrogen. In the dicarboxylic acid, it is currently preferred that R is hydrogen.

X, Y and Z represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate aryl thiocarbarnate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroantimonate, hypophosphite, iodate, periodate, metaborate, tetraaryl borate, tetraalkyl borate, tartrate, salicylate, succinate, citrate, ascorbate, saccharinate, amino acid, hydroxamic acid, thiotosylate, and anions of ion exchange resins, or systems where one or more of X, Y and Z are independently attached to one or more of the "R" groups, wherein n is an integer from 0 to 3. The preferred ligands from which X, Y and Z are selected include halide, organic acid, nitrate and bicarbonate anions.

As used herein, "R" groups means all of the R groups attached to the carbon atoms of the polyazamacrocycle, i.e., $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$ and $R_{20}$.

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms which optionally carries one or more substituents selected from (1) —$NR_{30}R_{31}$ wherein $R_{30}$ and $R_{31}$ are independently selected from hydrogen, alkyl, aryl or aralkyl; or $R_{30}$ is hydrogen, alkyl, aryl or aralkyl and $R_{31}$ is selected from the group consisting of —$NR_{32}R_{33}$, —OH, —$OR_{34}$,

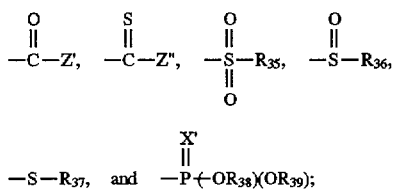

wherein $R_{32}$ and $R_{33}$ are independently hydrogen, alkyl, aryl or acyl, $R_{34}$ is alkyl, aryl or alkaryl, Z' is hydrogen, alkyl, aryl, alkaryl, —$OR_{34}$, —$SR_{34}$ or —$NR_{40}R_{41}$ wherein $R_{40}$ and $R_{41}$ are independently selected from hydrogen, alkyl, aryl or alkaryl, Z" is alkyl, aryl, alkaryl, —$OR_{34}$, —$SR_{34}$ or —$NR_{40}R_{41}$, $R_{35}$ is alkyl, aryl, —$OR_{34}$, or —$NR_{40}R_{41}$, $R_{36}$ is alkyl, aryl or —$NR_{40}R_{41}$, $R_{37}$ is alkyl, aryl or alkaryl, X' is oxygen or sulfur, and $R_{38}$ and $R_{39}$ are independently selected from hydrogen, alkyl or aryl;

(2) —$SR_{42}$ wherein $R_{42}$ is hydrogen, alkyl, aryl, alkaryl, —$SR_{34}$, —$NR_{32}R_{33}$,

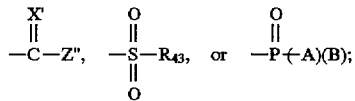

wherein $R_{43}$ is —OH, —$OR_{34}$ or —$NR_{32}R_{33}$, and A and B are independently —$OR_{34}$,— $SR_{34}$ or —$NR_{32}R_{33}$;

(3) 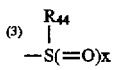

wherein x is 1 or 2, and $R_{44}$ is alkyl, aryl, alkaryl, —OH, —$OR_{34}$, —$SR_{34}$ or —$NR_{32}R_{33}$;

(4) —$OR_{45}$ wherein $R_{45}$ is hydrogen, alkyl, aryl, alkaryl, —$NR_{32}R_{33}$,

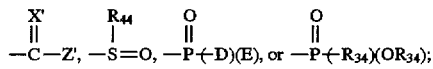

wherein D and E are independently —$OR_{34}$ or —$NR_{32}R_{33}$;

(5) 

wherein $R_{46}$ is —OH, —SH, —$OR_{34}$, —$SR_{34}$ or —$NR_{32}R_{33}$; or (6) amine oxides of the formula

provided $R_{30}$ and $R_{31}$ are not hydrogen; or (7)

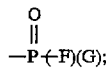

wherein F and G are independently —OH, —SH, —$OR_{34}$, —$SR_{34}$ or —$NR_{32}R_{33}$; or (8) halogen, cyano, nitro, or azido. Alkyl, aryl and alkaryl groups on the substituents of the above-defined alkyl groups may contain one additional substituent but are preferably unsubstituted. Examples of such radicals include, but are not limited to, methyl, ethyl, n-propyl, isopropyl, n-butyl, isobutyl, sec-butyl, tert-butyl, pentyl, isoamyl, hexyl, octyl, nonyl, decyl, dodecyl, tetradecyl, hexadecyl, octadecyl and eicosyl. The term "alkenyl", alone or in combination, means an alkyl radical having one or more double bonds. Examples of such alkenyl radicals include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans- 9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl. The term "alkynyl", alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl. The term "cycloalkyl", alone or in combination means a cycloalkyl radical containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and perhydronaphthyl. The term "cycloalkylalkyl" means an alkyl radical as defined above which is substituted by a cycloalkyl radical as defined above. Examples of cycloalkylalkyl radicals include, but are not limited to, cyclohexylmethyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentyl-methylhexyl, 1-(4-neopentylcyclohexyl)methylhexyl, and 1-(4-isopropylcyclohexyl)-methylheptyl. The term "cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl. The term "cycloalkenyl", alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cyclooctadienyl. The term "cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, 1-(1-cyclopenten-1-yl)hexyl, 6-(1-cyclohexen-1-yl)hexyl, 1-(1-cyclopenten-1-yl)nonyl and 1-(1-cyclohexen-1-yl)nonyl. The terms "alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentyl, 1-hexyl-cyclopentyl, 1-methyl-cyclohexyl, 1-(9-octadecenyl)cyclopentyl and 1-(9-octa-decenyl)cyclohexyl. The terms "alkylcycloalkenyl" and "alkenylcycloalkenyl" means a cycloalkenyl radical as defined above which is substituted by an alkyl or alkenyl radical as defined above. Examples of alkylcycloalkenyl and alkenylcycloalkenyl radicals include, but are not limited to, I-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl. The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl or cycloalkyl radical as defined above in which one hydrogen atom is replaced by an aryl radical as defined above, such as benzyl, 2-phenylethyl, and the like. The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. The term "saturated, partially saturated or unsaturated cyclic" means fused ring structures in which 2 carbons of the ring are also part of the fifteen-membered or sixteen membered macrocyclic ligand. The ring structure can contain 3 to 20 carbon atoms, preferably 5 to 10 carbon atoms, and can also contain one or more other kinds of atoms in addition to carbon. The most common of the other kinds of atoms include nitrogen, oxygen and sulfur. The ring structure can also contain more than one ring and can contain pendant substituents or functional groups as defined in the definition of alkyl groups herein. When the saturated, partially saturated or unsaturated cyclic is fused to the portion of the sixteen-membered ring having three carbons between nitrogens, the fused ring structure will contain 4 to 20 carbon atoms, preferably 5 to 10 carbon atoms, and can also contain one or more other kinds of atoms in addition to carbon. The term "saturated, partially saturated or unsaturated ring structure" means a ring structure in which one carbon of the ring is also pan of the fifteen-membered or sixteen-membered macrocyclic ligand. The ring structure can contain 3 to 20, preferably 5 to 10, carbon atoms and can also contain nitrogen, oxygen and/or sulfur atoms. The term "nitrogen containing heterocycle" means ring structures in which 2 carbons and a nitrogen of the ring are also pan of the fifteen-membered or sixteen-membered macrocyclic ligand. The ring structure can contain 2 to 20, preferably 4 to 10, carbon atoms, can be partially or fully unsaturated or saturated and can also contain nitrogen, oxygen and/or sulfur atoms in the portion of the ring which is not also pan of the fifteen-membered macrocyclic ligand. The term "organic acid anion" refers to carboxylic acid anions having from about 1 to about 18 carbon atoms. The term "halide" means chloride or bromide.

As utilized herein, the term "radicals attached to the α-carbon of α-amino acids" means "R" groups that are derived from the D or L forms of the amino acids Alanine, Aspartic acid, Arginine, Asparagine, Cysteine, Glycine, Glutamic acid, Glutamine, Histidine, Isoleucine, Leucine, Lysine, Methionine, Proline, Phenylalanine, Serine, Tryptophan, Threonine, Tyrosine, Valine and/or the "R" groups of unnatural α-amino acids such as alkyl, ethyl, butyl, tert-butyl; cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, nitrile, halo, thiol, sulfoxide, sulfone, sulfonic acid, sulfide, disulfide, phosphonic acid, phosphinic acid, phosphine oxides; sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof.

The diamines of the invention can be prepared by any conventional method such as those described in Jung, S-H and Kohn, K., *J. Am. Chem. Soc.*, 1985, 107, 2931–43 and Roskamp, E. J. and Pederson, S. F., *J. Am. Chem. Soc.*, 1987, 109, 3152–4 or are commercially available. Examples of suitable diamines include, but are not limited to, trans 1,2-diaminocyclohexane, 2,3-diaminobutane, 2,2-dimethyl, 1,3-diaminopropane, and 2,2-dimethyl, 1,2-diaminoethane.

The triamines of the invention can be prepared by any conventional method such as by coupling an N-protected amino acid with a vicinal diamine, e.g. ethylene diamine, 1R,2R-diaminocyclohexane and the like, followed by removing the protecting group, and further optionally reducing the carbonyl group. The middle nitrogen of this reduced triamine can then be protected if desired according to the method described in John D. Prush, Laura A. Birchenough, & Melissa S. Egbertson, Synth. Comm., Vol. 22, pp. 2357–60 (1992). Examples of suitable triamines include, but are not limited to, 4-(p-toluenesulfonyl)-1,4,7-triazaheptane and cis-1-N-(trans-2'-aminocyclohexyl)-diaminocyclohexane.

The dicarboxylic acids of the invention can be prepared by any conventional method such as those set out in the Examples. Examples of suitable dicarboxylic acids include, but are not limited to, those used in the Examples, such as 3,6-bis(p-toluenesulfonyl)-3,6-diazaoctanedioic acid.

The amount of diamine employed according to the invention can be conveniently expressed in terms of a molar ratio of diamine to dicarboxylic acid. Broadly, the molar ratio of diamine to dicarboxylic acid will be about 0.5:1 to about 2:1, preferably about 0.8:1 to about 1.2:1, and most preferably about 1:1.

The mount of triamine employed according to the invention can be conveniently expressed in terms of a molar ratio of triamine to dicarboxylic acid. Broadly, the molar ratio of triamine to dicarboxylic acid will be about 0.5:1 to about 2:1, preferably about 0.8:1 to about 1.2:1, and most preferably about 1:1.

As used herein, the term "coupling agent" means an agent capable of effecting the dehydrative coupling of a carboxylic acid group of the dicarboxylic acid with a terminal amine group of the diamine or triamine to form an amide bond between the reactants. The agents promote or facilitate the dehydrative coupling by activating the carboxylic acid group. Descriptions of such coupling agents are included in general text books of peptide chemistry, such as E. Schroder & K. L. Lubke, "The Peptides", Vol. 1, Academic Press, New York, N.Y., 1965, pp. 2–128; K. D. Kopple, "Peptides and Amino acids", W. A. Benjamin, Inc., New York, N.Y., 1966, pp. 33–51; and M. Bodanszky, "Principles of Peptide Synthesis", Springer-Verlag, Verlag, 1984, pp. 16–58. The selection of an appropriate coupling agent is within the skill in the art. Suitable coupling agents are selected from the group consisting of (1) phosphoryl azides (e.g. diphenylphosphoryl azide), (2) carbodiimides (e.g. N,N'-diisopropylcarbodiimide, N,N'-dicyclohexyl-carbodiimide and N-ethyl-N'-(γ-dimethylaminopropylcarbodiimide), (3) cyanamides (e.g. N,N-dibenzyl-cyanamide), (4) ketenimines, (5) isoxazolium salts (e.g. N-ethyl-5-phenyl-isoxazolium-3'-sulfonate), (6) monocyclic nitrogen containing heterocyclic amides of aromatic character containing 1 to 4 nitrogens in the ring such as imidazolides, pyrazolides and 1,2,4-triazolides (e.g. N,N'-carbonyldiimidazole and N,N-carbonyldi-1,2,4-triazole), (7) alkoxylated acetylene (e.g. ethoxyacetylene), (8) reagents which form a mixed anhydride with the carboxyl moiety of the dicarboxylic acid (e.g. ethylchloroformate, isobutylchloroformate, isobutyryl chloride, phosphorous trichloride, 1,2-phenylene phosphorochloridite, phosphorous oxychloride, diphenylchlorophosphate, N-ethoxycarbonyl-2-ethoxy-1,2-dihydroquinoline, bis(2-oxo-3-oxazolidinyl)phosphonic chloride and triphenylphosphite-imidazole), (9) nitrogen containing heterocyclic compounds having a hydroxy group on one ring nitrogen (e.g. N-hydroxyphthalimide, N-hydroxy-succinimide and 1-hydroxybenzotriazole) or carbonates thereof used in conjunction with a coupling agent from one of the other groups (e.g. 1-(3-dimethylaminopropyl)-3-ethylcarbodiimide hydrochloride and 1-hydroxybenzotriazole, and dicyclohexylcarbodiimide and 1-hydroxybenzotriazole, (10) reagents which form an active ester with the carboxyl moiety of the dicarboxylic acid (e.g. bromoacetonitrile, substituted phenols such as p-nitrophenol, pentachlorophenol, pentafluorophenol, hydroxybenzotriazole, N-hydroxysuccinimide, thiophenol, thiophenol and 2-hydroxypyridine), (11) benzotriazol-1-yloxytris(dimethylamino)phosphonium hexafluorophosphate, (12) re-dox based coupling agents (e.g. triphenylphosphine-2,2'-dipyridyldisulfide) and (13) mixtures thereof. The currently preferred coupling agents are diphenylphosphoryl azide, and 1-(3-dimethylaminopropyl)-3-ethylcarbodiimide hydrochloride with hydroxybenzotriazole.

The mount of coupling agent employed according to the invention can be conveniently expressed in terms of a molar ratio of coupling agent to dicarboxylic acid. Broadly, the molar ratio of coupling agent to dicarboxylic acid will be 2:1 to about 5:1, preferably 2:1 to about 3:1. If an anhydride of the dicarboxylic acid is used, the molar ratio of coupling agent to anhydride of the dicarboxylic acid will be 1:1 to about 3:1, preferably 1:1 to about 2:1.

Suitable bases for use in the invention are bases that are nonreactive with the coupling agent activated dicarboxylic acid and include trialkylamines, pyridines, imidazoles, and the like. Examples of suitable bases include, but are not limited to, triethylamine, pyridine, N-methylmorpholine and imidazole.

The amount of base employed according to the invention is the amount necessary to maintain the pH of the reaction medium to about 7 to about 9. The amount of base can be conveniently expressed in terms of a molar ratio of base to dicarboxylic acid. Broadly, the molar milo of base to dicarboxylic acid will be 2:1 to about 4:1, preferably 2:1 to about 3:1. If the dime or time is utilized as the diammonium salt which is converted in situ to the amine, the amount of base required will be increased to account for the base used to convert the diammonium salt to the amine.

Suitable solvents for use in the invention are non-reactive solvents in which the starting materials are at least partially soluble such as polar organic solvents. Examples of suitable solvents include, but are not limited to, dimethylformamide, dimethylacetamide, tetrahydrofuran, N-methyl-2-pyrrolidone, acetonitrile and mixtures thereof.

The amount of solvent employed according to the invention can be conveniently expressed in terms of molarity (moles/L or M). Broadly, the molarity will be about 0.001M to about 1M, preferably about 0.005 M to about 0.1M.

The temperature and time used in the process of the invention will depend on the particular reaction involved and will vary depending on factors such as coupling agent used, solvent used, concentration of the reaction mixture, and the solubility of the reactants. Based on the Examples herein, the temperature and time for any particular combination of reactants, solvent, coupling agent, concentration, etc. will be readily apparent to those skilled in the art. For example, a reaction temperature is about −30° C. to about 25° C. will generally be acceptable for most reactions. However, when the ester of the dicarboxylic acid is an alkyl ester an elevated reaction temperature is required, i.e. the reaction temperature will be within 40° C. of the boiling point of the solvent being used in the reaction. The time required will depend on the above factors as well as the temperature used.

The pentaazamacrocycles of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The commonly accepted mechanism of action of the manganese-based SOD enzymes involves the cycling of the manganese center between the two oxidation states (II,III). See J. V. Bannister, W. H. Bannister, and G. Rotilio, Crit. Rev. Biochem., 22, 111–180 (1987).

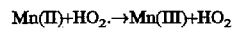  1)

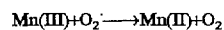  2)

The formal redox potentials for the $O_2/O_2^-$—and $HO_2/O_2$ couples at pH=7 are −0.33 v and 0.87 v, respectively. See A. E. G. Cass, in Metallopmteins: Part 1, Metal Proteins with Redox Roles, ed. P. Harrison, P. 121. Verlag Chemie (Weinheim, GDR) (1985). For the above disclosed mechanism, these potentials require that a putative SOD catalyst be able to rapidly undergo oxidation state changes in the range of −0.33 v to 0.87 v.

The complexes derived from Mn(II) and the general class of C-substituted [15]aneN$_5$ ligands described herein have all been characterized using cyclic voltammetry to measure their redox potential. The C-substituted complexes described herein have reversible oxidations of about +0.7 v (SHE). Coulometry shows that this oxidation is a one-electron process; namely it is the oxidation of the Mn(II) complex to the Mn(III) complex. Thus, for these complexes to function as SOD catalysts, the Mn(III) oxidation state is involved in the catalytic cycle. This means that the Mn(III) complexes of all these ligands are equally competent as SOD catalysts, since it does not matter which form (Mn(II) or Mn(III)) is present when superoxide is present because superoxide will simply reduce Mn(III) to Mn(II) liberating oxygen.

The manganese complexes of the present invention can be utilized to treat numerous inflammatory disease states and disorders. For example, reperfusion injury to an ischemic organ, e.g., reperfusion injury to the ischemic myocardium, surgically-induced ischemia, inflammatory bowel disease, rheumatoid arthritis, osteoarthritis, psoriasis, organ transplant rejections, radiation-induced injury, oxidant-induced tissue injuries and damage, atherosclerosis, thrombosis, platelet aggregation, stroke, acute pancreatitis, insulin-dependent diabetes mellitus, disseminated intravascular coagulation, fatty embolism, adult and infantile respiratory distress, metastasis and carcinogenesis.

Activity of the compounds or complexes of the present invention for catalyzing the dismutation of superoxide can be demonstrated using the stopped-flow kinetic analysis technique as described in Riley, D. P., Rivers, W. J. and Weiss, R. H., "Stopped-Flow Kinetic Analysis for Monitoring Superoxide Decay in Aqueous Systems," *Anal. Biochem.*, 196, 344–349 (1991), which is incorporated by reference herein. Stopped-flow kinetic analysis is an accurate and direct method for quantitatively monitoring the decay rates of superoxide in water. The stopped-flow kinetic analysis is suitable for screening compounds for SOD activity and catalytic activity of the compounds or complexes of the present invention for dismutating superoxide, as shown by stopped-flow analysis, correlate to treating the above disease states and disorders.

Total daily dose administered to a host in single or divided doses may be in mounts, for example, from about 1 to about 100 mg/kg body weight daily and more usually about 3 to 30 mg/kg. Unit dosage compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral is used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, granules and gels. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds which are known to be effective against the specific disease state that one is targeting for treatment.

The compounds or complexes of the invention can also be utilized as MRI contrast agents. A discussion of the use of contrast agents in MRI can be found in patent application Ser. No. 08/397,469, which is incorporated by reference herein.

Contemplated equivalents of the general formulas set forth above for the compounds and derivatives as well as the intermediates are compounds otherwise corresponding thereto and having the same general properties such as tautomers of the compounds and such as wherein one or more of the various R groups are simple variations of the substituents as defined therein, e.g., wherein R is a higher alkyl group than that indicated, or where the tosyl groups are other nitrogen or oxygen protecting groups or wherein the O-tosyl is a halide. Anions having a charge other than 1, e.g., carbonate, phosphate, and hydrogen phosphate, can be used instead of unions having a charge of 1, so long as they do not adversely affect the overall activity of the complex. However, using unions having a charge other than I will result in a slight modification of the general formula for the complex set forth above. In addition, where a substituent is designated as, or can be, a hydrogen, the exact chemical nature of a substituent which is other than hydrogen at that position, e.g., a hydrocarbyl radical or a halogen, hydroxy., amino and the like functional group, is not critical so long as it does not adversely affect the overall activity and/or synthesis procedure. Further, it is contemplated that manganese(III) complexes will be equivalent to the subject manganese(II) complexes.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative; and not limitative of the remainder of the disclosure in any way whatsoever.

EXAMPLES

All reagents were used as received without purification unless otherwise indicated. All NMR spectra were obtained on a Varian VXR-300 or VXR-400 nuclear magnetic resonance spectrometer. Qualitative and quantitative mass spectroscopy was run on a Finnigan MAT90, a Finnigan 4500 and a VG40-250T using m-nitrobenzyl alcohol(NBA) or m-nitrobenzyl alcohol/LiCl (NBA+Li); or dithiothreitol/ dithioerythritol (DTT/DTE), under fast atom bombardment (FAB) or chemical ionization (CI) conditions. Melting points (mp) are uncorrected.

The following abbreviations relating to amino acids and their protective groups are in accordance with the recommendation by IUPAC-IUB Commission on Biochemical Nomenclature (Biochemistry, 11, 1726 (1972)) and common usage.

| TFA | Trifluoroacetate |
|---|---|
| DMF | Dimethylformamide |
| HOBT.H$_2$O | 1-Hydroxy-(1H)-benzotriazole monohydrate |
| EDC.HCl | 1-(3-Dimethylaminopropyl)-3-ethylcarbodiimide hydrochloride |
| TEA | Triethylamine |
| DMSO | Dimethylsulfoxide |
| THF | Tetrahydrofuran |

-continued

| DPPA | Diphenylphosphoryl azide |
|---|---|
| DMPU | Dimethylpropyleneurea |
| c | concentration, g/cc |
| DME | 1,2-Dimethoxyethane |

Example 1

1A. Synthesis of trans-5,6-Dimethyl-3,8-dioxo-1,10, 13-tris(p-toluenesulfonyl)-1,4,7,10,13-pentaazacyclopentadecane A solution of D,L-2,3-diaminobutane dihydrochloride containing 20% of the meso isomer (8.05 g, 50.0 mmole), 3,6,9-tris(p-toluenesulfonyl)-3,6,9-triazaundecanedioic acid prepared as in EP Patent Application 0 524 161 A1 (34.1 g, 50.0 mmole) and triethylamine (20.2 g, 200 mmole) in degassed anhydrous DMF (10.0 L) under a dry argon atmosphere was cooled to −45° to −50° C. Diphenylphosphorylazide (33.0 g, 120 mmole) was then added dropwise over 5 minutes and the resulting solution was allowed to warm to room temperature while stirring for 14 h. The solvent was then removed in vacuo and residual DMF was removed by co-evaporation with H$_2$O (2×1.0 L). The residue was dissolved in acetonitrile (300 ml) and methanol (700 ml) was added in portions as the product crystallized. The solid was filtered, washed with methanol and dried to give 17.2 g of colorless needles. The filtrate was concentrated to an oil and residual DMF was removed by co-evaporation with H$_2$O in vacuo. The residue was dissolved in a mixture of ethyl acetate (500 ml) and H$_2$O (500 ml) and the layers were separated. The ethyl acetate was washed with 0.1N HCl (2×200 ml), saturated NaHCO$_3$ solution (2×200 ml) and saturated NaCl solution (500 ml), at which point a large mass of crystals formed in the ethyl acetate layer. The mixture was filtered and the crystals were washed with ethyl acetate and dried to give an additional 3.4 g of the product as colorless needles. Recrystallization from CHCl$_3$— methanol gave 21.7 g (59% yield) of the racemic product as colorless needles: mp 250°–253° C. dec.; $^1$H NMR (CDCl$_3$, 400 MHz) δ 1.21 (d, J=5.6 Hz, 6H), 2.45 (s, 9H), 3.20 (m, 4H), 3.39 (m, 2H), 3.46 (d, J=16.4 Hz, 2H), 3.55 (m, 2H), 3.89 (m, 2H), 3.91 (d, J=16.4 Hz, 2H), 6.55 (d, J=6.2 Hz, 2H), 7.35 (m, 6H), 7.71 (m, 6H); $^{13}$C NMR (CDCl$_3$, 100 MHz) δ 18.51, 21.58, 49.80, 50.70, 51.61, 54.49, 127.55, 127.68, 129.97, 130.09, 133.97, 134.33, 143.96, 144.47, 168.20; FAB mass spectrum (NBA+Li) m/z 740 [M +H]$^+$.

1B. Synthesis of trans-2,3-Dimethyl-1,4,7,10,13-pentaazacyclopentadecane

To a stirred suspension of trans-5,6-dimethyl-1,10,13-tris (p-toluenesulfonyl)-1,4,7,10,13-pentaazacyclopentadecane-3,8-dione prepared as in example 1A (21.6 g, 29.4 mmole) in anhydrous THF (590 ml) under a dry argon atmosphere was added a solution of 1.0M LiAlH$_4$ in THF (368 ml, 368 mmole) dropwise over 5 minutes. The resulting clear yellow solution was refluxed for 32 h (by which time it had become heterogeneous) and was then cooled to 0° C. The mixture was quenched by the dropwise addition of 10% Na$_{SO4}$ (18 ml) while cooling in an ice bath. The mixture was then filtered under argon and the solids were refluxed for 30 minutes with anhydrous THF (1.0 L). Following filtration, the solids were refluxed with THF (1.0 L) and the mixture was filtered again. The filtrates were evaporated in vacuo and redissolved in THF, combined and filtered. The solvent was removed in vacuo and the residue was dissolved in hot acetonitrile (50 ml). The cloudy solution was filtered and the filtrate was concentrated to a volume of 20 ml. Crystallization was initiated by briefly touching a piece of dry ice to the outside of the flask. As crystallization proceeded, the flask was slowly cooled to –20° C. Following filtration, the crystals were purified by recrystallization from acetonitrile to give 1.87 g (26.1% yield) of the product as colorless needles: mp (under argon) 81°–83° C.; $^1$H NMR ($C_6D_6$, 300MHz) δ 0.88 (m, 6H), 1.46 (br s, 5H), 2.10 (m, 2H), 2.34 (m, 2H), 2.52 (m, 10H), 2.64 (m, 2H), 2.76 (m, 2H); x3C NMR (Co, D6, 100 MHz) δ 17.31, 47.29, 48.47, 48.87, 49.34, 59.46; CI mass spectrum ($CH_4$) m/z 244 [M+H]$^+$.

1C. Synthesis of [Manganese(II) dichloro (D,L-2,3-Dimethyl- 1,4,7,10,13-pentaazacyclopentadecane)]

To a stirred solution of anhydrous $MnCl_2$ (383 mg, 3.04 mmol) in anhydrous methanol was added D,L-2,3-dimethyl-1,4,7,10,13-pentaazacyclopentadecane prepared as in example 1B (740 mg, 3.04 mmol). The solution was refluxed for 1h, and then the solvent was removed in vacuo. The residue was dissolved in hot THF and filtered through Celite™. The filtrate was concentrated in vacuo to a volume of 5 ml. Ethyl ether was added to the warm solution resulting in the precipitation of a white solid which was collected by filtration. After drying in vacuo, a yield of 0.81 g (72%) was obtained; FAB mass spectrum (NBA) m/z (relative intensity) 333/335 (100/30) [M–Cl]$^+$; Anal. Calcd. for $C_{12}H_{29}N_5Cl_2Mn$: C, 39.03; H, 7.92; N, 18.97; Cl, 19.20. Found: C, 38.95; H, 7.96; N, 18.88; Cl, 19.25.

Example 2

2A. Preparation of Dimethyl 2S, 10S -bis(tert-butylthiomethyl)-4, 8-dioxo-6-p-toluenesulfonyl-3,6,9-triazaundecanoate.

N-p-Toluenesulfonyliminodiacetic acid (7.73 g, 26.9 mmol), prepared according to example 5A, was placed in a 500 ml round bottomed flask equipped with a magnetic stirbar and under argon atmosphere. DMF (300 ml) was added to the flask, and the flask was cooled in an ice-water bath. HOBT.$H_2O$ (8.25 g, 53.9 mmol) was added followed by EDC.HCl (12.38 g, 64.6 mmol). After 5 min, S-t-butyl-L-cysteine methyl ester hydrochloride (prepared from S-t-butyl-L-cysteine following: Pastuszak, J. J., Chimiak, A. *J. Org. Chem.* 1981, 46, 1868–1873) was added to, the solution followed by triethylamine (7.51 ml, 53.9 mmol). The mixture turned a light orange color and precipitate began to form. The mixture was stirred and allowed to slowly warm to room temperature. After ~16 h, the mixture was concentrated to ~75 ml volume in vacuo. Ethyl acetate (EtOAc) (300 ml) and aq. $NaHCO_3$ (200 ml) were added to the slurry. The layers were separated and the aqueous layer was extracted twice with 1130 ml of EtOAc. The EtOAc layers were combined and washed with 0.5N $NaHSO_4$ (200 ml), sat. $NaHCO_3$ (100 ml), 2×100 ml water, brine (100 ml), dried over $MgSO_4$, filtered and concentrated to a pale yellow foam, 15.0 g (88%). $^1$H NMR ($CDCl_3$, 300 MHz) δ 1.28 (s, 18H), 2.40 (s, 3H), 2.86–3.01 (m, 4H), 3.73 (s, 6H), 3.90 (s, 4H), 4.73 (dd, J=5.7, 13.2 Hz 2H), 7.29 (d, J=8.1 Hz, 2H), 7.39 (d, J=7.5 Hz, 2H), 7.75 (d, J=8.4 Hz, 2H); $^{13}$C NMR ($CDCl_3$, 75 MHz) δ 21.6, 31.0, 30.8, 42.7, 52.1, 52.5, 52.6, 127.9, 129.8, 134.7, 144.3, 167.8, 170.8.

2B. Preparation of 2S,10S-Bis(tert-butylthiomethyl)-4,8-dioxo-6-p-toluenesulfonyl-3,6,9-triazaundecanoic acid NaOH (1.84 g, 46.0 mmol) in 50 ml of water was slowly added to a cooled solution of dimethyl 2S, 10S-bis(tert-butylthiomethyl)-4,8-dioxo-6-p-toluenesulfonyl-3,6,9-triazaundecanoate (14.68 g, 23.16 mmol) in 100 ml of THF. After 1.5 h, aq. HCl (23.2 mmol) was added to the cooled solution and the THF was removed in vacuo. The mixture was then neutralized with the addition of 23 ml of 1N HCl. EtOAC was added and the pH of the aqueous layer was monitored. Additional 1N HCl was added to bring the aqueous layer to pH=2.5 and the layers were separated. The aqueous layer was extracted twice with 100 ml of EtOAc. The EtOAc layers were combined, washed with 50 ml of water and 100 ml of brine, dried over $MgSO_4$, filtered and concentrated to a dry foam, 13.7 g (98%). $^1$H NMR (DMSO-$d_6$, 300 MHz) δ 1.24 (s, 18H), 2.37 (s, 3H), 2.68–2.87 (m, 4H), 3.94 (s, 4H), 4.34 (dd, J=7.1, 13.7 Hz, 2H), 7.36 (d, J=8.1 Hz, 2H), 7.68 (d, J=8.1 Hz, 2H), 8.69 (d, J=8.1 Hz, 2H), 12.87 (br s, 2H). $^{13}$C NMR (DMSO-$d_6$, 100 MHz) δ 21.0, 29.6, 30.6, 42.2, 50.6, 52.8, 127.2, 129.5, 135.6, 143.2, 168.b, 171.4.

2C. Preparation of 6S, 145-Bis(tert-butylthiomethyl)-2R, 3R-cyclohexano-5,8,12,15-tetraoxo-10-p-toluenesulfonyl-1,4,7,10,13-pentaazacyclopentadecane HOBT-$H_2O$ (6.88 g, 44.9 mmol) and EDC.HCl (10.33 g, 53.9 mmol) were added to a cooled solution (0° C) of 2S, 10S-bis(tert-butylthiomethyl)-4,8-dioxo-6-p-toluenesulfonyl-3,6,9-triazaundecanoic acid (13.60 g, 22.4 mmol) in 4 L of DMF. After 15 min, 1R,2R-diaminocyclohexane in 30 ml of DMF was added to the cooled solution. The solution was stirred under argon atmosphere and allowed to slowly warm to room temperature. After ~16 h, the solution was concentrated in vacuo to a slurry and EtOAc and aq. $NaHCO_3$ (~100 ml) were added. The layers were combined and separated. The aqueous layer was extracted with EtOAc, then all EtOAc layers were combined, washed with 0.5N $NaHSO_4$, saturated $NaHCO_3$, water (2 times), brine, dried over $MgSO_4$, filtered and concentrated to yield crude solid. Pure product was isolated by trituration with EtOAc, as a white solid, weight 8.6 g (56%). $^1$H NMR (300 MHz, DMSO-$d_6$) δ 1.00 –1.39 (m, 22H), 1.52–1.69 (m, 2H), 1.69–1.88 (m, 2H), 2.39 (s, 3H), 2.50–2.75 (m, 4H), 3.32–3.52 (m, 2H), 3.66 (d, J=17.3 Hz, 2H), 3.86 (d, J=17.1 Hz, 2H), 4.09–4.24 (m, 2H), 7.44 (d, J=8.3 Hz, 2H), 7.76 (d, J=8.1 Hz, 2H), 7.79–7.90 (m, 2H), 8.59 (d, J=7.1 Hz, 2H). $^{13}$C NMR (100 MHz, DMSO-$d_6$) δ 21.0, 24.4, 29.0, 30.7, 31.9, 42.0, 52.1, 52.7, 54.1, 127.4, 129.9, 134.8, 143.8, 168.2, 168.8; FAB mass spectrum (NBA+Li) m/z 690 [M+Li]$^+$, 696 [M–H+2Li]$^+$.

2D. Preparation of 2S,9S-Bis(tert-butylthiomethyl)5R,6R-cyclohexano-1,4,7, 10, 13-pentaazacyclopentadecane A 500 ml round bottomed flask equipped with a magnetic stirbar and condenser under argon atmosphere was charged with 68,14S-bis(tert-butylthiomethyl)-2R, 3R-cyclohexano-5,8,12,15-tetraoxo-10-p-toluenesulfonyl-1,4,7,10,13-pentaazacyclopentadecane (2.88 g, 4.21 mmol) in 100 ml of THF. $LiAlH_4$ (105 ml, 0.5M in DME, 52.5 mmol) was added to the mixture which was then heated to reflux. After ~16 h, the reaction was allowed to cool to room temperature then was cooled in an ice-water bath and quenched by the addition of 2.0 ml of water, 2.0 ml of 15% NaOH (aq.), and 6.0 ml of water. Tiff was added to the mixture and the suspension was filtered under inert atmosphere several times. The filtrates were concentrated and the residue crystallized from acetonitrile to give 0.60 g of product (30%). $^1$H NMR ($CDCl_3$, 300 MHz) δ 0.88–1.08 (m, 2H), 1.15–1.30 (m, 2H), 1.29 (s, 18H), 1.64–1.79 (m, 2H), 1.94–2.25 (m, 11H), 2.45–2.89 (m, 12H), 2.90–3.05 (m, 2H), 3.06–3.18 (m, 2H); $^{13}$C ($CDCl_3$, 75 MHz) δ 24.9, 30.9, 31.2, 31.7, 42.0, 45.8, 48.5, 51.6, 58.0, 63.2; Exact mass (M+H)$^+$: calcd, 474.3664; found, 474.3686 ($C_{24}H_{52}N_5S_2$).

2E. Preparation of [Manganese(II) dichloro (2S,9S-t-butylthiomethyl-5R,6R-cyclohexano-1,4,7,10,13-pentaazacyclopentadecane)]

2S ,9S-Bis(tert-butylthiomethyl)-5R,6R-cyclohexano-1,4,7,10,13-pentaazacyclopenta-decane (269 mg, 0.568 mmol) was added to a hot methanol (MeOH) solution containing 90 mg of $MnCl_2$. The solution was stirred overnight and then was evaporated to dryness. The resultant oil was dissolved in hot THF, filtered through Celite™, and evaporated to dryness to yield 275 mg (81%). FAB mass spectrum m/z 563 [M–Cl⁻]⁺. Catalytic rate constant for the dismutation of superoxide at pH 8.1 and 21° C., $k_{cat}$=1.29× $10^7$ mol⁻¹sec⁻¹.

Example 3

3A. Synthesis of Ethyl 2R,3R-cyclohexano-1,4-diaza-5R-methyl-1-(p-toluenesulfonyl)-6-hexanoate To a stirred solution of N-p-toluenesulfonyl-1R,2R-diaminocyclohexane, prepared as in U.S. Patent Application Serial No. 08/397,469, (9.98 g, 37.2 mmole) in anhydrous methylene chloride ($CH_2Cl_2$) (250 ml) under a dry argon atmosphere was added triethylamine (3.76 g, 37.2 mmole) and the resulting solution was cooled to 0° C. A solution of ethyl L-lactate trifluoromethanesulfonate (9.30 g, 37.2 mmole) in anhydrous $CH_2Cl_2$ (50 ml) was added dropwise to the solution over 45 minutes, maintaining the temperature at 0° C. The mixture was then stirred for 16 h while allowing it to warm to room temperature. $CH_2Cl_2$ (500 ml) was added and the solution was washed with saturated $NaHCO_3$ solution (500 ml), $H_2O$ (500 ml) and saturated NaCl solution (250 ml) and was dried ($MgSO_4$). After filtration, the solvent was removed in vacuo to give 14.3 g of crude product as a yellow oil: ¹H NMR ($CDCl_3$, 300 MHz) δ 0.94 (m, 1H), 1.10–1.34 (m, 9H), 1.51–1.68 (m, 3H), 1.86 (m, 1H), 2.20 (m, 2H), 2.44 (s, 3H), 2.52 (m,.1H), 3.29 (q, J=6.8 Hz, 1H), 4.15 (q, J=7.1 Hz, 2H), 5.30 (br s, 1H), 7.31 (d, J=8.1 Hz, 2H), 7.76 (d, J=8.3 Hz, 2H); ¹³C NMR ($CDCl_3$, 75 MHz) δ 14.17, 19.76, 21.53, 24.10, 24.73, 32.24, 32.34, 54.82, 58.05, 59.71, 60.95, 127.28, 129.61, 137.10, 143.22, 176.10; FAB mass spectrum (DTT/DTE) m/z 369 [M+H]⁺.

3B. Synthesis of Ethyl 4-benzyloxycarbonyl-2R,3R-cyclohexano-1,4-diaza-5R-methyl-1-(p-toluenesulfonyl)-6-hexanoate To a stirred solution of ethyl 2R,3R-cyclohexano-1,4-diaza-5R-methyl-1-(p-toluenesulfonyl)-6-hexanoate prepared as in Example 3A (14.2 g of crude product) in THF (250 ml) was added 2N NaOH (20 ml, 40.0 mmole) slowly at 0° C. Benzyl chloroformate (6.94 g, 40.7 mmole) was added in portions and the mixture was allowed to warm to room temperature. At 2 h, additional benzyl chloroformate (2.00 g, 11.7 mmole) was added, the pH was adjusted to 8–9 with 2N NaOH and the mixture was stirred for 18 h. After filtration, the solvent was removed in vacuo to give an oil which rapidly crystallized. The crude product was dissolved in a mixture of ethyl acetate (500 ml) and $H_2O$ (500 ml) and the layers were separated. The ethyl acetate layer was washed with $H_2O$ (2×500 ml), saturated NaCl solution and was dried ($MgSO_4$). The solvent was removed in vacuo to give 26.7 g of a colorless oil. Following trituration of the oil with hexanes, the product crystallized into a solid mass. Recrystallization from $CH_2Cl_2$— hexanes gave 16.8 g (90.2% yield) of the product as colorless prisms: mp 119°–121° C.; ¹H NMR (DMSO-$d_6$, 1130° C., 400 MHz) δ 0.98–1.18 (m, 6H), 1.40 (d, J=7.0 Hz, 3H), 1.48 (br d, J=12.3 Hz, 1H), 1.59 (br d, J=11.0 Hz, 1H), 1.70 (br s, 1H), 1.86 (br s, 1H), 2.33 (s, 3H), 3.14 (br q, J=7.3 Hz, 1H), 3.63 (br s, 1H), 3.92–4.01 (m, 3H), 4.87–497 (m, 2H), 6.88 (d, J=7.2 Hz, 1H), 7.28–7.35 (m, 7H), 7261 (d, J=8.1 Hz, 2H); ¹³C NMR (DMSO-$d_6$, 100° C., 100 MHz) δ 14.33, 16.50, 21.35, 24.82, 25.53, 29.78, 33.71, 53.87, 58.35, 61.05, 65.63, 66.76, 126.83, 127.91, 128.09, 128.65, 129.74, 137.06, 140.32, 142.56, 154.50, 172.02; FAB mass spectrum (NBA+ Li) m/z 509 [M+H]⁺.

3C. Synthesis of 4-Benzyloxycarbonyl-2R,3R-cyclohexano-1,4-diaza-5R-methyl-1-(p-toluenesulfonyl)-6-hexanoic acid To a stirred suspension of ethyl 4-benzyloxycarbonyl-2R, 3R-cyclohexano-1,4-diaza-5R-methyl-1-(,p-toluenesulfonyl)-6-hexanoate prepared as in Example 3B (11.7 g, 23.2 mmole) was slowly added 2N NaOH (17.4 ml, 34.8 mmole) and the resulting clear solution was stirred for 3 h at room temperature and then at 50° C. for another 2 h. The methanol was removed in vacuo, $H_2O$ (250 ml) was added and the aqueous solution was washed with ethyl ether (500 ml). The pH was then adjusted to 2 with 1N HCl and the product was extracted into ethyl acetate (3×500 ml). The extracts were combined, washed with $H_2O$ (250 ml), saturated NaCl solution (250 ml) and were dried ($MgSO_4$). The solvent was removed in vacuo to give 10.76 g (97.8% yield) of the product as a white solid: ¹H NMR (DMSO-$d_6$) shows a doubling of peaks at 25° C. due to conformational isomers; ¹H NMR (DMSO-$d_6$, 100° C, 300 MHz) δ 1.02–1.20 (m, 3H), 1.39 (d, J=6.9 Hz, 3H), 1.39–1.61 (m, 2H), 1.89 (m, 3H), 2.34 (s, 3H), 3.17 (m, 1H), 3.56 (m, 1H), 3.97 (q, J=6.9 Hz, 1H), 4.90 (m, 2H), 7.03 (br.s, 1H), 7.27–7.37 (m, 7H), 7.61 (d, J=7.9 Hz, 2H), 12.33 (br s, 1H); ¹³C NMR (DMSO-$d_6$, 100° C, 100 MHz) δ 15.99, 20.79, 24.14, 24.95, 29.51, 33.18, 53.38, 56.86, 63.97, 66.19, 126.35, 127.14, 127.43, 128.10, 129.18, 136.53, 139.34, 142.02, 154.09, 173.55; FAB mass spectrum (NBA - HCl) m/z 475 [M+H]⁺.

3D. Synthesis of Methyl 4-benzyloxycarbonyl-2R,3R-cyclohexano-5R,8R-dimethyl-6-oxo- 1-(p-toluenesulfonyl)-1,4,7-triazanonanoate To a stirred solution of 4-benzyloxycarbonyl-2R,3R-cyclohexano-1,4-diaza-5R-methyl-1-(p-toluenesulfonyl)-6-hexanoic acid prepared as in example 3C (10.6 g, 22.6 mmole), 1-hydroxybenzotriazole monohydrate (3.66 g, 23.9 mmole) and triethylamine (5.25 g, 51.9 mmole) in anhydrous DMF (250 ml) under a dry argon atmosphere was added 1-ethyl-3-(3-dimethyl-aminopropyl)carbodiimide hydrochloride (5.19 g, 27.1 mmole) and the mixture was stirred at room temperature for 30 minutes. Then, D-alanine methyl ester hydrochloride (3.47 g, 24.83 mmole) was added and the mixture was stirred at room temperature for 17 h. The solvent was then removed in vacuo and the residue was dissolved in a mixture of ethyl acetate (500 ml) and $H_2O$ (500 ml). The layers were separated and the ethyl acetate layer was washed with 0.1N HCl (2×250 ml), saturated $NaHCO_3$ solution (2×250 ml), saturated NaCl solution (250 ml) and was dried ($MgSO_4$). The solvent was removed in vacuo to give 11.8 g (93.4% yield) of a pale yellow solid: ¹H NMR (DMSO-$d_6$, 100° C., 400 MHz) δ 1.02–1.94 (m, 14H), 2.31 (s, 3H), 3.05 (m, 1H), 3.22 (m 1H), 3.64 (s, 3H), 4.33–4.82 (m, 4H), 7.22: 7.36 (m, 7H), 7.58 (d, J=7.5 Hz 2H), 7.82 (br s, 1H), 8.13 (br s, 1H); ¹³C NMR (DMSO-$d_6$, 100 MHz) δ 16.15, 16.75, 20.78, 24.07, 24.96, 30.62, 34.43, 47.88, 51.78, 53.46, 54.80, 59.39, 6.24, 126.37, 127.21, 127.58, 128.20, 129.18, 136.51, 139.39, 141.90, 154.70, 72.38, 173.06; FAB mass specmam (NBA - Li) m/z 566 [M+Li]⁺.

3E. Synthesis of Dimethyl 6-benzyloxycarbonyl-4R,5R-cyclohexano-7R, 10R-dimethyl-8-oxo-3-(p-toluenesulfonyl)-3,6,9-triazaundecanedioate To a stirred solution of methyl 4-benzyloxycarbonyl-2R, 3R-cyclohexano-5R,8R-dimethyl-6-oxo-1-(p-toluenesulfonyl)-1,4,7-triazanonanoate prepared as in example 3D (10.2 g, 18.2 mmole) in anhydrous DMF (100 ml) under a dry argon atmosphere was added methyl bromoacetate (5.58 g, 36.5 mmole) and the solution was cooled to 0° C. Sodium hydride (547 mg, 80% in oil, 18.2mmole)

was then added and mixture was allowed to warm to room temperature while stirring. At 2 h, additional NaH (547 mg, 80% in oil, 18.2 mmole) and methyl bromoacetate (5.58 g, 36.5 mmole) were added at 0° C. and the mixture was stirred at 0° C. At 5.25 h, more NaH (274 mg, 80% in oil, 9.12 mmole) and methyl bromoacetate (2.79 g, 18.2 mmole) were added at 0° C. and the mixture was stirred for another 30 minutes while warming to room temperature. The mixture was then quenched by pouring into $H_2O$ (500 ml). The solvent was then removed in vacuo and the residue was dissolved in a mixture of ethyl acetate (1 L) and $H_2O$ (1L). The layers were separated and the ethyl acetate layer was washed with $H_2O$ (2×1 L) and saturated NaCl solution (500 ml) and was dried ($MgSO_4$). The solvent was removed in vacuo to give 12.4 g of a pale yellow solid: FAB mass spectrum (NBA - Li) m/z 638 [M +Li]$^+$. This exude product was not purified and was hydrolyzed in Example 3F.

3F. Synthesis of 6-Benzyloxycarbonyl-4R,5R-Cyclohexano-7R, 10R-dimethyl-8-oxo-3-(p-toluenesulfonyl)-3,6,9-triazaundecanedioic acid To a solution of dimethyl 6-benzyloxycarbonyl-4R,5R-cyclohexano-7R, 10R-dimethyl-8-oxo-3-(p-toluenesulfonyl)-3,6,9-triazaundecanedioate prepared as in Example 3E (12.3 g, 19.5 mmole) in anhydrous methanol (250 ml) was slowly added a solution of 2N sodium hydroxide (30 ml, 60.0 mmole) and the bright yellow solution was stirred at room temperature for 2 h and then at 50° C. for 2 h. Then, 10 ml of 2N sodium hydroxide was added and the solution was stirred at 50° C. for 2.5 h at which time the reaction was complete. The solvent was removed in vacuo and the residue was dissolved in $H_2O$ (500 ml). The aqueous solution was washed with ethyl ether (2×500 ml) and the pH was adjusted to 1 with 1N HCl. After saturating the aqueous mixture with NaCl, the product was extracted into ethyl acetate (3×500 ml), the extracts were combined, dried over $MgSO_4$, and the solvent was removed in vacuo. Crystallization of the crude product from ethyl acetate—ethyl ether resulted in the formation of a gelatinous precipitate. The solid was filtered, washed with ethyl ether and dried to give 5.98 g (50.7% for two steps) of the product as a white solid: mp 155° C.; $^1$H NMR (DMSO-$d_6$, 100° C., 400 MHz) δ 0.90–2.10 (m, 14 H), 2.36 (s, 3H), 3.70–4.35 (m, 6H), 5.03 (m, 2H), 7.29–7.35 (m, 7H), 7.69 (d, J=7.3 Hz, 2H), 8.00 (br s, (1H), 12.20 (br s, 2H); $^{13}$C NMR (DMSO-$d_6$, 1130° C., 100 MHz) δ 17.26, 21.37, 21.46, 25.14, 25.39, 30.17, 31.40, 46.20, 49.15, 58.91, 59.70, 67.00, 127.95, 128.05, 128.47, 129.73, 129.84, 137.15, 138.12, 143.56, 155.53, 171.22, 171 31,173.80; FAB mass speclamm (NBA - Li) m/z (relative intensity) 610 (74) [M+Li]$^+$, 616 (1130) [M+2Li-H]$^+$, 622 (87) [M+3Li-2H]$^+$.

3G. Synthesis of 4-Benzyloxycarbonyl-2R,3R, 11 R, 12R-bis(cyclohexano)-5R, 8R-dimethyl-6,9,14-trioxo-1,4,7, 10,13-pentaaza-1-p-toluenesulfonyl-cyclopentadecane To a stirred solution of 6-benzyloxycarbonyl-4R,5R-cyclohexano-7R,10R-dimethyl-8-oxo-3-(p-toluenesulfonyl) -3,6,9-triazaundecanedioic acid prepared as in Example 3F (5.93 g, 9.83 mmole) and 1R,2R-diaminocyclohexane (1.12 g, 9.8 mmole) in degassed, anhydrous DMF (2.00 L) under a dry argon atmosphere was added triethylamine (1.99 g, 19.7 mmol). The solution was cooled to −45° C. and diphenylphosphorylazide (6.49 g, 23.8 mmole) was then added dropwise over 5 min. The solution was stirred for 22 h while allowing to warm slowly to room temperature. The solution was then stored at −35° C. for an additional 44 h. The solvent was removed in vacuo and residual DMF was removed by co-evaporation with $H_2O$ (2×300 mi). The residue was dissolved in ethyl acetate (1.5 L), was washed with 0.01N HCl (2×500 ml), saturated NaHCO$_3$ (2×500 ml) and saturated NaCl (500 ml), and was dried (MgSO$_4$). The solvent was removed in vacuo to give the crude product as a yellow solid which was purified by flash chromatography (silica gel, CHCl$_3$:MeOH 98:2 (v/v)) to give 3.40 g (50.7%) of the macrocycle as a 3:5 mixture of 2 conformations: $^1$H NMR (DMSO-$d_6$, 400 MHz) δ 0.64 (m, 1.1H), 0.79 (d, J=6.5 Hz, 1.91H), 1.50–1.88 (m, 19H), 2.41 (s, 3H), 3.26 (m, 1H), 3.44 (d, J=15.6 Hz, 1H), 3.61–3.82 (m, 2.2H), 3.87 (quint, J=6.7 Hz, 0.6H), 3.96–4.07 (m, 2.2 H), 4.20 (quint, J=6.7 Hz, 1H), 5.00 (d, J=12.9 Hz, 0.35H) 5.06 (d, J=12.6 Hz, 0.65H), 5.22 (d, J=13.2 Hz, 0.35H), 5.24 (d, J=12.6 Hz, 0.65H), 6.90 (d, J=6.4Hz, 0.6H), 7.09 (d, J=5.9 Hz, 0.4H), 7.28–7.45 (m, 7.4H), 7.53(d, J=6.2 Hz, 0.6H), 7.94 (m, 2H), 8.55 (m, 1H); $^{13}$C NMR (DMSO-$d_6$, 100 MHz) δ 16.05, 17.88, 18.63, 18.93, 20.89, 23.75, 23.90, 24.30, 24.37, 24.68, 24.72, 27.37, 30.21, 30.27, 31.27, 31.37, 31.50, 32.36, 46.07, 46.11, 50.56, 50.66, 51.47, 51.88, 52.56, 52.80, 57.04, 57.15, 57.75, 57.86, 58.10, 65.82, 66.02, 79.08, 127.17, 127.36, 127.49, 127.58, 127.61, 127.89, 128.06, 128.08, 128.09, 129.66, 136.08, 136,13, 136.91, 137.20, 143.58, 143.61, 154.79, 155.64, 169.59, 170.02, 170.95, 171.15, 171.64; FAB mass spectrum (NBA+Li) m/z 688 [M+Li]$^+$.

3H. Synthesis of 2R,3R,11R,12R-Bis(cyclohexano)-5R,8R-dimethyl -6,9,14-trioxo-1,4,7,10,13-pentaaza-1-p-toluenesulfonyl-cyclopentadecane To a stirred solution of 4-benzyloxycarbonyl-2R,3R, 11R, 12R-bis(cyclohexano)-5R,8R-dimethyl-6,9,14-trioxo-1,4,7, 10,13-pentaaza-1-p-toluenesulfonyl-cyclopentadecane prepared as in example 3G (3.30 g, 4.84 mmole) in a mixture of methanol (60 ml) and H$_2$O (30 ml) under an argon atmosphere was added ammonium formate (968 mg) and palladium black (484 mg) and the resulting mixture was refluxed for 1 h and then stirred for 21 h at room temperature. The catalyst was removed by filtration and the solvent was removed in vacuo to give 2.69 g of a white solid. Residual ammonium formate was decomposed by addition of palladium black (1 g) to a solution of the crude product in methanol (50 ml) and refluxing for 17 h. Following filtration and removal of the solvent in vacuo, the product was purified by flash chromatography (silica gel, CHCl$_3$:MeOH:aq. NH$_4$OH, 97.5:2.5:1 (v/v/v) to give 2.50 g (94.3% yield) of the macrocycle as a colorless solid: $^1$H NMR (C$_6$D$_6$, 70° C., 400 MHz); δ 0.65–1.40 (m, 18 H), 1.60 (m, 1H), 1.69 (d, J=7.0 Hz, 3H), 1.90 (s, 3H), 2.31 (br m, 1H), 2.85 (br s, 1H), 3.23–3.46 (m, 3H), 3.58–3.81 (m, 3H), 4.21 (m, 1H), 6.92 (d, J=7.9 Hz, 2H), 7.03 (br, s, 1H), 7.32 (br d, J=6.0 Hz, 1H), 7.54 (br s, 1H), 7.67 (d, J=8.1 Hz, 2H); $^{13}$C NMR (C$_6$D$_6$, 70° C., 100 MHz) δ 17.79, 18.25, 20.68, 24.30, 24.46, 24.82, 25.36, 28.71, 32.06, 33.15, 49.25, 52.38, 53.17, 54.26, 54.43, 55.47, 64.60, 127.34, 129.63, 138.26, 143.43, 169.48, 172.81, 175.79; FAB mass spectrum (NBA+Li) m/z 554 [M+Li]$^+$.

3I. Synthesis of 2R,3R, 11 R, 12R-Bis(cyclohexano)-5R, 8R-dimethyl- 1,4,7,10,13-pentaazacyclopentadecane To a stirred solution of 2R,3R, 11R, 12R-bis (cyclohexano)-5R,8R-dimethyl-6,9,14-trioxo-1,4,7,10,13-pentaaza-1-p-toluenesulfonyl-cyclopentadecane prepared as in Example 3H (2.45 g, 4.47 mmole) in anhydrous THF (90 ml) was added a solution of 1.0M LiAlH$_4$ (45.0 ml, 45.0 mmole) dropwise over 5 minutes and the bright yellow solution was refluxed for 15 h (by which time it had become heterogeneous). The mixture was then diluted by the addition of THF (200 ml) and was quenched by the dropwise addition of a 10% Na$_2$SO$_4$ solution (10 ml) while cooling in an ice bath. The mixture was then filtered and the solids were stirred with anhydrous THF (300 ml) and filtered again. The solids were then refluxed with anhydrous THF (300 ml) for 2 h and stirred overnight at room temperature. Following filtration, the solvent was removed from the extracts which were combined and extracted with ethyl ether. The solvent was removed from the yellow filtrate and the residue was dried by azeotroping with toluene (50 ml) and then hexanes (50 ml) to give 1.67 g of a viscous yellow oil. The product was dissolved in hexanes, leaving behind a small amount of oily byproduct. The solution was concentrated in vacuo to give 1.59 g of a yellow oil. The crude product was purified by crystallization from acetonitrile to give 324 mg (20.6% yield) of colorless needles: mp (under argon) 98°–100° C.; $^1$H NMR ($C_6D_6$, 400 MHz) δ 0.68 (m, 2H), 0.94 (d, J=6.2 Hz, 3H), 0.97– 1.11 (m, 8H), 1.12 (d, J=6.4 Hz, 3H), 1.56 (m, 4H), 1.90–2.15 (m, 10H), 2.34–2.50 (m, 6H), 2.66 (m, 1H), 2.76 br d, J=9.9 Hz, 1H), 2.94 (br m, 1H), 3.01 (br s, 2H); $^{13}$C NMR ($C_6D_6$, 100 MHz) δ 17.31, 19.10, 25.33, 25.43, 25.64, 25.80, 31.73, 31.96, 32.30, 32.39, 46.74, 47.79, 52.19, 53.61, 54.71, 57.30, 61.10, 62.38, 62.99; FAB mass spectrum (NBA - HCl) m/z 352 [M+H]$^+$.

3J. Synthesis of [Manganese(II)dichloro(2R,3R,11R,12R-bis(cyclohexano)-5R, 8R-dimethyl-1,4,7,10,13-pentaazacyclopentadecane)]

To a stirred solution of $MnCl_2$ (72 mg, 0.57 mmole) in anhydrous methanol was added 2R,3R,11R, 12R-bis(cyclohexano)-5R,8R-dimethyl-1,4,7,10,13-pentaazacyclopentadecane prepared as in Example 31 (201 mg, 0.572 mmole) under a dry nitrogen atmosphere and the solution was refluxed for 1 h. The solvent was removed in vacuo and THF (30 ml) was added. To the suspension was added ethanol (1 ml), causing the solid to dissolve. The solution was filtered through Celite™ and concentrated to a volume of 5 ml. Ethyl ether (40 ml) was then added to the hot solution and the solution was allowed to cool to room temperature while standing for 3 days. The colorless needles were filtered to give 172 mg (35.9% yield) of the product: FAB mass spectrum (NBA) m/z (relative intensity) 443/441 (100/32) [M–Cl]$^+$; Anal. Calcd. for $C_{20}H_{43}N_5MnCl_2$: C, 50.10; H, 9.04; N, 14.61. Found: C, 50.31; H, 8.61; N, 14.66.

Example 4

4A. Preparation of 2,3-trans-cycloheptano-5, 15-dioxo-7, 10, 13-tris(p-toluenesulfonyl)-1,4,7,10,13-pentaazacyclopentadecane.

Two 5 L round bottomed flasks were each charged with 1,2-diaminocycloheptane dihydrochloride (3.49 g, 17.35 mmol), prepared according to (1) from cycloheptanedioxime (2), triethylamine (9.67 ml, 69.4 mmol), and 3,6,9-tris-(p-toluenesulfonyl)-3,6,9-triazaundecanedioic acid (11.83 g, 17.35 mmol) in 3.5 L of degassed DMF. A dry ice-acetone bath was placed around the flask and the solution was cooled to −40° C. Diphenylphosphoryl azide (8.97 ml, 41.6 mmol) was added to the stirred solution over 10 min. The reaction was allowed to slowly warm to room temperature over 16 h. The reaction mixtures were then concentrated together, and the residue was taken up in methylene chloride and washed several times with water. Crystals formed in the methylene chloride layer and were collected to yield 4.27 g of trans isomer. The filtrate was washed with aqueous $NaHCO_3$, aqueous $KHSO_4$, water, brine, dried over $MgSO_4$, filtered, and concentrated slightly. A second and third crop of crystals were collected from methylene chloride yielding 8.94 g and 4.48 g of trans isomer. The remaining filtrate was concentrated and purified by column chromatography using 1% MeOH in $CH_2Cl_2$ as eluent. Fractions were collected to yield 1.0 g of pure cis isomer and 2.7 g of both c/s and trans isomers. A total of 21.4 g of both isomers was collected (79.5%) including. 17.7 g of pure trans isomer (66%). 2,3-trans-cycloheptano-5,15-dioxo-7,10,13-tris-(p-toluenesulfonyl)-1,4,7,10,13-pentaazacyclopentadecane: $^1$H NMR (400 MHz, DMSO-$d_6$): δ 1.64–1.30 (m, 10H), 2.39 (s, 6H), 2.40 (s, 3H), 3.15–2.90 (m, 8H), 3.48 (d, J=16.1 Hz, 2H), 3.75–3.65 (m, 2H), 3.97 (d, J=16.1 Hz, 2H), 7.35–7.31 (m, 6H), 7.50 (d, J=8.1 Hz, 2H), 7.70 (d, J=8.1 Hz, 4H), 7.92 (d, J=7.8 Hz, 2H). $^{13}$C NMR (100 MHz, DMSO): δ 20.88, 23.96, 27.99, 31.94, 46.29, 46.51, 50.45, 54.03, 126.67, 127.16, 129.55, 129.90, 134.82, 136.13, 143.21, 143.61, 166.01.

References (1) Belcher, R.; Hoyle, W.; West, T. S. *J. Chem. Soc.* 1961, 667–670.

(2) Vander Haar, R. W.; Voter, R. C.; Banks, C. V. *J. Org. Chem.* 1949, 14, 836–838.

4B. Preparation of 2,3-trans-cycloheptano- 1,4,7,10,13-pentaazacyclopentadecane

Following the procedure used in Example 2D, 2,3-trans-cycloheptano-5,15-dioxo-7,10,13-tritosyl-1,4,7,10,13-pentaazacyclopentadecane (6.00 g, 7.75 mmol) was reduced with $LiAlH_4$ in DME to yield 2,3-trans-cycloheptane-1,4,7,10,13-pentaazacyclopentadecane. Recrystallization from $CH_3CN$ provided 808 mg of fine needle crystals (37%). $^1$H NMR (400 MHz, $CDCl_3$): δ 1.31–1.46 (m, 4H), 1.48–1.56 (m, 2H), 1.60–1.71 (m, 2H), 1.74–1.84 (m, 2H), 2.01 (br s, 5H), 2.18–2.25 (m, 2H), 2.45–2.54 (m, 2H), 2.57–2.77 (m, 10H), 2.79–2.86 (m, 2H), 2.91–2.98 (m, 2H). $^{13}$C NMR (100 MHz, $CDCl_3$): δ 64.98, 48.73, 48.37, 47.98, 46.86, 29.82, 28.50, 24.02. Anal. Calcd for $C_{15}H_{33}N_5$: C, 63.56; H, 11.73; N, 4.71. Found: C, 63.46; H, 11.66; N, 24.72.

Example 5

5A. N-p-Toluenesulfonyliminodiacetic acid

Iminodiacetic acid (200 g, 1.50 mol) was dissolved in water (3 L) and sodium hydroxide (180 g, 4.5 mol) was added in small portions with stirring. After stirring for 15 minutes, p-toluenesulfonyl chloride (286.5 g, 1.5 mol) was added in small portions. The reaction mixture was heated to 80° C. for one hour, giving a clear solution. At the end of this time, the reaction solution was cooled in an ice bath to 10°—15° C., and concentrated HCl (110 ml) was added, precipitating the product as a white solid. This solid was filtered and washed with cold water, then dried in a vacuum oven at 55° C., giving 207.7 g (0.723 mol, 48.2% yield): mp 195°–196° C . (lit.* mp 191° C.); $^1$H NMR (DMSO-$d_6$, 300 MHz) δ 2.38 (s, 3H), 3.66 (s, 4H), 7.39 (d, J=8.7 Hz, 2H), 7.65 (d, J=8.1 Hz); $^{13}$C NMR (DMSO-$d_6$, 75 MHz) δ 20.90, 53.98, 126.55, 129.79, 136.70, 143.17, 171.77.

*J. M. Lehn, J. Simon, J. Wagner, Nouv. J. Chim. (1977) 1, 77–84.

5B. Synthesis of Dimethyl 25,10S-dimethyl-6-p-toluenesulfonyl-4,8-dioxo-3,6,9-triazaundecanedioate N-Tosyliminodiacetic acid (28.76 g, 100.1 mmol) was dissolved in N,N-dimethylacetamide (1 L). The solution was degassed and placed under argon. Hydroxybenzotriazole hydrate (41.30 g, 269.8 mmol), L-alanine methyl ester hydrochloride (35.20 g, 252.1 mmol) and triethyl amine (35.4 ml, 254 mmol) were added, then 1-ethyl-3-(3-dimethylaminopropyl)carbodiimide hydrochloride (51.8 g, 70.2 mmol). The heterogeneous reaction was stirred overnight. The solvent was then removed under reduced pressure. Ethyl acetate (500 ml) was added, and water (250 ml) was added with swirling, to dissolve the residue. The organic phase was washed with saturated $NaHCO_3$ (2×250 ml), 1M HCl (2×250 ml), then saturated NaCl (250 ml). After drying (Na₂SO₄), the solution was concentrated to a white foam, 36.5 g, 79.8 mmol, 79.7% yield; mp 144°–146° C.; $^1$H NMR (CDCl₃, 400 MHz) δ 1.39 (d, J=7.3 Hz, 6H), 2.41 (s, 3H), 3.71 (s, 6H), 3.87 (s, 4H), 4.50 (quint, J=7.4 Hz, 2H), 7.30 (d, J=8.1 Hz, 2H), 7.61 (d, J=7.3 Hz, 2H), 7.40 (d, J=8.3 Hz, 2H); $^{13}$C NMR (CDCl₃, 100 MHz) δ 17.60, 21.57, 48.28, 52.43, 2.63, 127.76, 129.75, 134.63, 144.29, 167.80, 173.04. HRMS. Calcd for C₁₉H₂₇N₃O₈S: 457.1519. Found: 457.1538.

5C. Synthesis of 2S,10S-Dimethyl-6-p-toluenesulfonyl-4,8-dioxo-3,6,9-triazaundecanedioic acid Dimethyl 2S,10S-dimethyl-6-p-toluenesulfonyl-4,8-dioxo-3,6,9-triazaundecanedioate (25.0 g, 54.6 mmol) was dissolved in 1:1 THF: methanol (300 ml) and stirred while sodium hydroxide solution (2.5M, 75 ml, 187.5 mmol) was added. After stirring overnight, tlc (silica, developed in 1:9 methanol: dichloromethane) showed that some starting material was still present ($R_f$=0.46), so additional sodium hydroxide solution (40 ml, 100 mmol) was added, and the reaction mixture was heated for 20 minutes at 40° C., and stirred one hour longer at room temperature. At the end of this time, water (150 ml) was added, and the resulting mixture was washed with ether (3×60 ml). The pH of the aqueous layer was adjusted to about 2 by the addition of 1M KHSO₄. The aqueous layer was extracted with ethyl acetate (3×100 ml). After drying (MgSO₄), the ethyl acetate extract was snipped off and the residue was recrystallized from ethyl acetate—ether, giving the diacid as a white solid, 17.86 g (41.6 mmol, 76% yield): mp 119°–120° C.; $^1$H NMR (DMSO-d₆, 400 MHz) δ 1.27 (d, J=7.25 Hz, 6H), 2.40 (s, 3H), 3.91 (AB quartet, J=17.3 Hz, Δv=21.1 Hz, 4H), 4.19 (quintet, J=7.1 Hz, 2H), 7.40 (d, J=8.1 Hz, 2H), 7.71 (d, J=7.8 Hz, 2H), 8.70 (d, J=7.25 Hz, 2H); $^{13}$C NMR (DMSO-d₆, 75 MHz) δ 17.11, 20.91, 47.49, 51.20, 127.17, 129.55, 135.43, 143.37, 167.91, 173.54; HRMS. Calcd for C₁₇H₂₃N₃O₈S: 429.1206. Found: 429.1195. Elemental analysis. Calcd: C, 47.55%; H, 5.40%; N, 9.78%. Found: C, 47.42%; H, 5.41%; N, 9.75%.

5D. Synthesis of 2S,9S-Dimethyl-5R,6R-cyclohexano-3,8,11,15-tetraoxo-13-p-toluenesulfonyl-1,4,7,10,13-pentaazacyclopentadecane To a solution of 2S,10S-dimethyl-6-p-toluenesulfonyl-4,8-dioxo-3,6,9-triazaundecanedioic acid (9.66 g, 22.49 mmol) in degassed DMF (4.5 L), triethyl amine (6.2 ml, 45 mmol) and 1R,2R-diaminocyclohexane (2.57 g, 22.5 mmol) were added. The stirred reaction mixture was cooled to −20° C., and diphenylphosphoryl azide (11.6 ml, 53.8 mmol) was added. After stirring overnight, during which time the reaction reached room temperature, the solvent was removed under reduced pressure. The residue was dissolved in ethyl acetate, and washed with sodium bicarbonate (1:1 saturated solution: water), potassium hydrogen sulfate (5%), and saturated sodium chloride solution. After drying over MgSO₄ and filtration, the solvent was removed under reduced pressure, and the residue was recrystallized from acetonitrile as a white crystalline solid, 9.41 g, 18.54 mmol, 82.4% yield. mp 360° C. (dec); $^1$H NMR (DMSO-d₆, 400 MHz) δ 1.16, 1.21 (d +m, J=7.0 Hz, 10H), 1.63 (br s, 2H), 1.90 (m, 2H), 2.42 (s, 3H), 3.41 (br s, 2H), 3.65 (d, J=16.4 Hz, 2H), 3.91 (d, J=16.4 Hz, 2H), 4.22 (quint, J=7.3 Hz, 2H), 7.47 (d, J=8.1 Hz, 2H), 7.73, 7.77 (d+br s, J=8.1 Hz, 4H), 8.57 (d, J=7.8 Hz, 2H); $^{13}$C NMR (DMSO-d₆, 100 MHz) δ 16.93, 20.91, 24.26, 31.24, 48.44, 52.79, 52.88, 54.84, 127.11, 129.95, 134.33, 143.87, 168.46, 171.59. HRMS. Calcd for C₂₃H₃₃N₅O₆S: 507.2151. Found: 507.2145. Elemental analysis. Calcd: C, 54.42%; H, 6.55%; N, 13.80%. Found: C, 54.15%; H, 6.55%; N, 13.56%.

5E. Synthesis of 2S,9S-Dimethyl-5R,6R-cyclohexano-1,4,7,10,13-pentaazacyclopentadecane 2S,9S-Dimethyl-5R,6R-cyclohexano-3,8,11,15-tetraoxo-13-p-toluenesulfonyl-1,4,7,10,13-pentaazacyclopentadecane (7.0 g, 13.8 mmol) was suspended in 1,2-dimethoxyethane (DME, 350 ml) under argon, and lithium aluminum hydride (0.5M in DME, 275 ml, 138 mmol) was added rapidly via cannula. The resulting mixture was refluxed overnight, then allowed to cool to room temperature. The reaction mixture was then cooled to −40° C. and water (5.2 ml) was very cautiously and slowly added over a 12 minute period, followed by 15% NaOH (5.2 ml), and water (15.7 ml). THF (400 ml) was added after about 20 minutes and stirring was continued. The cold bath was removed fifteen minutes later. After stirring a few minutes longer, stirring was stopped and the mixture was allowed to settle. The supernatant was decanted via cannula into an argon filled flask, and was subsequently filtered using a cannula tipped (paper) filter. Additional THF was added to the white residue, and stirring was started. After a few hours, the supernatant was removed as before, and filtered. This process was repeated once more using 1 L THF. The combined THF filtrates were stripped under reduced pressure. The residue was extracted with hot hexane, and filtered under argon, and the stripped residue was recrystallized from dry acetonitrile, 2.74 g, 9.21 mmol, 66.8% yield, as a white crystalline solid, mp (under N₂) 179°–180° C.; $^1$H NMR (C₆D₆, 400 MHz) δ 0.85 (m, 2H), 0.96 (d, J=6.2 Hz, 6H), 1.11 (m, 2H), 1.40–1.66 (m, 4H), 1.71–2.08 (m, 9H), 2.42 (m, 2H), 2.55–2.66 (m, 6H), 2.72–2.83 (m, 4H); $^{13}$C NMR (C₆D₆, 100 MHz) δ 19.34, 25.49, 32.41, 46.92, 49.03, 54.09, 55.28, 63.82; HRMS. Calcd for C₁₆H₃₅N₅: 297.2892. Found: 297.2889. Elemental analysis. Calcd: C, 64.60%; H, 11.86%; N, 23.54%. Found: C, 64.55%; H, 11.77%; N, 23.54%.

Example 6

6A. Synthesis of cis-5,6-Cyclohexano-3,8-dioxo-1,10,13-tris(p-toluenesulfonyl)-1,4,7,10,13-pentaazacyclopentadecane A stirred solution of 3,6,9-tris(p-toluenesulfonyl)-3,6,9-triazaundecanedioic acid (15.3 g, 22.5 mole), cis-1,2-diaminocyclohexane (2.57 g, 22.5 mole) and triethylamine (4.55 g, 45.0 mmole) in degassed anhydrous DMF (4.50 L) under a dry argon atmosphere was cooled to −40° C. and diphenylphosphorylazide (14.9 g, 54.0 mmole) was added dropwise over 10 minutes. The mixture was allowed to warm to room temperature while stirring for 15 h and the solvent was removed in vacuo. The residue was dissolved in ethyl acetate (2.0 L), washed with 0.1N HCl (2×500 ml), saturated NaHCO₃ solution (2×500 ml) and saturated NaCl solution (500 ml), and was dried (MgSO₄). After filtration, the solution was concentrated to a volume of 250 ml and ethyl ether was added periodically as the crystallization progressed. The crystals were filtered, washed with ether and dried to give 15.0 g of crude product. Recrystallization from CH₂Cl₂—methanol and flash chromatographic purification of the filtrate (silica gel, CHCl₃:MeOH, 97.5:2.5 (v/v)) gave a total of 11.54 g (67.5% yield) of the macrocycle: mp 256°–257° C.; $^1$H NMR (CDCl₃, 400 MHz) δ 1.53 (br s, 6H), 1.78 (br s, 2H), 2.45 (s, 9H), 3.18 (m, 2H), 3.37 (m, 2H), 3.46 (d, J=16.7 Hz, 2H), 3.51 (m, 4H), 3.82 (d, J=16.9 Hz, 2H), 4.16 (br s, 2H), 6.84 (d, J=7.3 Hz, 2 H), 7.36 (d, J=8.3 Hz, 6H), 7.71 (d, J=8.3 Hz, 4H), 7.75 (d, J=8.3 Hz, 2H); $^{13}$C NMR (CDCl₃, 100 MHz) δ 21.61, 22.04, 28.14, 49.46, 49.58, 51.52, 54.60, 127.61, 127.75, 130.00, 130.11, 133.64, 135.29, 144.07, 144.60, 168.20; FAB mass spectmam (NBA - Li) m/z 766 [M+Li]⁺.

6B. Synthesis of cis-2,3-Cyclohexano-1,4,7,10,13-pentaazacyclopentadecane

To a stirred suspension of cis-5,6-cyclohexano-1,10,13-tris(p-toluenesulfonyl)-1,4,7,10,13-pentaazacyclopentadecane-3,8-dione prepared as in example 6A (13.5 g, 17.8 mole) in anhydrous THF (340 ml) under a dry argon atmosphere was added a solution of 1.0M LiAlH$_4$ in THF (222 ml, 222 mmole) dropwise over 30 minutes. The yellow homogeneous solution was refluxed for 17 h, by which time it had become heterogeneous. The mixture was then cooled to room temperature in a water bath and H$_2$O (7.1 ml) was added dropwise over 5 minutes, followed 5 minutes later by a 15% solution of NaOH (7.1 ml) and then 5 minutes later by H$_2$O (20.7 ml). The slurry was filtered and the solids were refluxed with THF (2×500 ml) for 30 minutes and filtered. Then the solids were stirred with a mixture of THF (250 ml) and MeOH(250 ml) at room temperature for 2 days and then refluxed for 3 h. The mixture was filtered and the residue was redissolved in THF and filtered again. The filtrates were combined and the solvent was removed in vacuo. The crude product was crystallized from acetonitrile to give 2.22 g (46.3%) of the product which contains 5% of the trans isomer. Recrystallization from hexanes and then acetonitrile reduced the amount of trans isomer to 2%, giving 1.92 g (32.4% yield) of the product as colorless needles: mp (under argon) 115–116° C; $^1$H NMR (C$_6$D$_6$, 400 MHz) δ 8 1.24 (m, 4H), 1.43 (br s, 5H), 1.70 (m, 4H), 2.43 m, 2H), 2.49–2.62 (m, 14 H), 2.68 (m, 2H); $^{13}$C NMR (CDCl$_3$, 100 MHz) δ 22.21, 27.75, 46.49, 48.15, 48.58, 48.97, 57.24; CI mass spectrum (CH$_4$) m/z 270 [M+H]$^+$.

Example 7

7A. 1,7-Bis(p-toluenesulfonyl)-2R,3R-cyclohexano-5-oxo-1,4,7-triazaheptane

N-p-Toluenesulfonyl-1R,2R-diaminocyclohexane (15 g, 55.9 mmol) was dissolved in DMF (550 ml), and triethylamine (9.4 ml, 61.1 mmol) and N-p-toluenesulfonyl glycine (15.4 g, 67.1 mmol) were added. The solution was cooled to −20° C., and diphenylphosphoryl azide (14.5 ml, 67.2 mmol) was added dropwise over 8 minutes. The reaction was allowed to warm to room temperature overnight. After removal of solvent under reduced pressure, the residue was dissolved in dichloromethane (200 ml) and washed with water (50 ml), sodium bicarbonate (1:1 saturated: water, 50 ml), 5% KHSO$_4$ (50 ml), then saturated NaCl (50 ml). The organic layer was dried (MgSO$_4$), filtered, and the solvent was removed under reduced pressure, and the residue Was recrystallized from dichloromethane-hexanes, 21.76 g, (45.37 mmol), 81% yield, as a white crystalline solid, mp 96°–97° C.; $^1$H NMR (CDCl$_3$, 400 MHz) δ 1.0–1.27 (m, 4H), 1.52–1.71 (m, 3H), 1.81–1.92 (br s, 1H), 2.38, 2.39 (2 s, 6H), 2.96 (m, 1H), 3.4–3.68 (m, 3H), 5.68 (d, J=7.8 Hz, 1H), 5.98 (t, J=6.3 Hz, 1H), 6.76 (d, J=8.9 Hz), 7.26 (d, J=7.8 Hz, 4 H), 7.72 (m, 4H); $^{13}$C NMR (CDCl$_3$, 100 MHz) δ 21.51, 24.50, 24.74, 31.92, 33.21, 46.09, 52.98, 57.95, 126.88, 127.24, 129.69, 129.86, 136.19, 138.55, 143.24, 143.78, 169.26; HRMS. Calcd for C$_{22}$H$_{29}$N$_3$O$_5$S$_2$: 479.1548. Found: 479.1549.

7B. Preparation of Dimethyl 3,9-bis(p-toluenesulfonyl)-4R,5R-cyclohexano-7-oxo-3,6,9-triazaundecanedioate 1,7-Bis(p-toluenesulfonyl)-2R,3R-cyclohexano-5-oxo-1,4,7-triazaheptane (5.0 g, 10.4 mmol) was dissolved in DMF (100 ml) under argon, and methyl bromoacetate was added (5.9 ml, 62.3 mmol). The reaction progress was monitored by tlc (on silica, developed in 10% methanol, 90% dichloromethane, R$_f$=0.57 for starting material, R$_f$=0.65 for diester product) and additional reagents were added as necessary. After cooling the solution to 0° C., sodium hydride (1.06 g, 44.2 mmol) was added with stirring. At the end of the addition, the ice bath was removed, and the reaction was stirred for one hour at room temperature. Heating was begun in a water bath, for 2.75 h, at an internal temperature of 35° to 40° C. Twenty minutes before the end of the heating period, additional methyl bromoacetate (2 ml, 21.1 mmol) was added. The reaction was stirred overnight at room temperature. The reaction was placed in an ice bath, and additional sodium hydride (0.26 g, 10.8 mmol) and methyl bromoacetate (1.0 ml, 10.6 mmol) were added, and the ice bath was removed. Three hours later, water (200 ml) was added to the reaction mixture, and the solvents were removed under reduced pressure. The residue was dissolved in ethyl acetate (150 ml), washed with water (3×80 ml), saturated sodium chloride solution (50 ml), and dried over MgSO$_4$. After filtration, the solvent was removed under reduced pressure. The product was used in the next step without further purification. MS m/z (relative intensity) 630 (100, [M+Li$^+$]).

7C. Preparation of 3,9-Bis(p-toluenesulfonyl)-4R,5R-cyclohexano-7-oxo-3,6,9-triazaundecanedioic acid Dimethyl 3,9-bis(p-toluenesulfonyl)-4R,5R-cyclohexano-7-oxo-3,6,9-triazaundecandioate, from the previous preparation, without additional purification, was dissolved in methanol (40 ml) and stirred while aqueous sodium hydroxide (2.5N, 25 ml, 62.5 mmol) was added. After stirring overnight, tlc indicated the presence of starting material: Additional sodium hydroxide solution (8 ml of 2.5M, 20 mmol) was added and the reaction flask was heated in a 50° C. water bath for 4.5 hours. At the end of this time, the solvent was removed under reduced pressure. Water was added and the resulting solution was washed twice with ether (30 ml) and the pH was adjusted to about 3 by the addition of 1M KHSO$_4$. The aqueous layer was extracted with ethyl acetate (3×50 ml). The combined ethyl acetate layers were dried over MgSO$_4$, filtered and the solvent was removed under reduced pressure. The residue was chromatographed twice on silica, eluting with 8% methanol, 1% acetic acid, 91% dichloromethane. The fractions containing product (R$_f$=0.29, on a silica plate, developed in 1% acetic acid, 10% methanol, 89% dichloromethane) were combined and chromatographed on silica initially eluting with 1% acetic acid, 2% methanol, 97% dichloromethane, and later eluting with 1% acetic acid, 4% methanol, 95% dichloromethane. Product containing fractions were combined, and the solvents removed under reduced pressure. Toluene was added to the residue, and the resulting mixture was concentrated, and the process was repeated. The product was obtained as an off-white solid, 4.58 g, 7.69 mmol, 73.7% (for two steps): mp 265°–268° C. (dec). $^1$H NMR (CD$_3$OD, 400 MHz) δ 1.00–1.38 (m, 4H), 1.46 (m, 1H), 1.60 (m, 2H), 1.96 (m, 1H), 2.40 (s, 3H), 2.42 (s, 3H), 3.33 (m, 1H), 3.68 (m, 1H), 3.75–4.2 (m, 7H), 7.33 (d, J=8.1 Hz, 2H), 7.39 (d, J=8.1 Hz, 2H), 7.75 (d, J=8.1 Hz, 2H), 7.78 (d, J=8.3 Hz, 2H). Electrospray mass spectrum m/z (relative intensity) 618 (100, [M+Na]$^+$), 596 (25, [M+H]$^+$).

7D. Preparation of 2R,3R,8R,9R-Bis(cyclohexano)-3,13-bis(p-toluenesulfonyl)-6,11,15-trioxo-1,4,7,10,13-pentaazacyclopentadecane Triethylamine (1.12 ml, 8.05 mmol), 1R,2R-diaminocyclohexane (0.46 g, 4.02 mmol), and 7-oxo-3,9-bis(p-toluenesulfonyl)-4R,5R-cyclohexano-3,6,9-triazaundecanedioic acid (2.4 g, 4.0 mmol) were dissolved in degassed DMF (1000 ml) and cooled to −20° C. under argon. Diphenylphosphoryl azide (2.08 ml, 9.66 mmol) was added, and the reaction was stirred overnight, rising to room temperature. The solvent was removed under reduced pressure. Dichloromethane was added to the residue, precipitating a white powder. The filtrate was stripped, then dissolved in dichloromethane (200 ml) and washed successively with single portions of sodium bicarbonate, 5% potassium bisulfate, and saturated sodium chloride solution. After drying (MgSO$_4$) and filtering, the solvent was removed under reduced pressure. Recrystallization from acetonitrile gave successive crops totalling 1.62 g, 2.40 mmol, 60% yield: white crystals; mp 298°–299° C.; $^1$H NMR (CDCl$_3$, 400 MHz) δ 0.57 (m, 2H), 1.11–1.48(m, 6H), 1.55–1.89(m, 5H), 1.98–2.52(s+m, 9H),3.15 (d,J=14.5 Hz, 1H), 3.41–3.76 (m, 6H), 4.14 (m, 1H), 4.26 (d, J=18.3 Hz, 1H), 4.63 (d, J=17.2 Hz, 1H), 5.93 (d, J=9.9 Hz), 6.28 (d, J=5.4 Hz, 1H), 7.27 (m, 4H), 7.53 (d, J=8.1 Hz, 1H), 7.75 (d, J=8.1 Hz, 1H), 8.64 (d, J=8.6 Hz, 1H); $^{13}$C NMR (CDCl$_3$, 100 MHz) δ 21.51, 24.23, 24.34, 24.89, 25.52, 28.48, 31.91, 32.75, 33.68, 46.80, 50.78, 51.43, 53.60, 54.21, 54.44, 62.04, 126.64, 127.81, 129.86, 130.11, 135.77, 136.24, 144.13, 144.17, 167.32, 168.17, 168.27; MS m/z (relative intensity) 680 (100 [M+Li]$^+$); Elemental analysis. Calcd: C, 57.04%; H, 6.43%; N, 10.39%. Found: C, 56.99%; H, 6.57%; N, 10.27%.

Example 8

8A. Preparation of Dimethyl 2R-methyl-3-azapentandioate.

L-Alanine methyl ester hydrochloride (24.24 g, 173.7 mmol) in 600 ml of DMF was placed in a 2L round bottomed flask under argon atmosphere. Triethylamine (48.4 ml, 347 mmol) was added to the solution and precipitate began to form. Methyl bromoacetate (17.0 ml, 173.7 mmol) was added dropwise to the mixture, and the mixture was stirred at room temperature. After 16 h, the mixture was concentrated, EtOAc and water were added and the layers were combined and separated. The EtOAc layer was washed with water and brine, dried over Na$_2$SO$_4$, filtered and concentrated to yield 20.0 g of light tan oil (66%). Dimethyl 2S-methyl-3-azapentandioate was prepared from D-alanine methyl ester hydrochloride, in the same manner. $^1$H NMR (CDCl$_3$, 300 MHz) δ 1.30 (d, J=6.9 MHz, 3H), 2.03 (s, 1H), 3.30–3.49 (m, 3H), 3.68 (s, 6H).

8B. Preparation of Dimethyl 2S-methyl-3-p-toluenesulfonyl-3-azapentanoate.

Dimethyl 2S-methyl-3-azapentanoate (19.7 g, 112 mmol) was gradually added to a mixture of p-toluenesulfonylchloride (24.0 g, 126 mmol) in 150 ml of pyridine. The resulting light orange solution was placed in an oil bath at 50 ° C. and stirred for 1 h. The mixture was allowed to cool to room temperature then was cooled in an ice-water bath. Water (250 ml) was added to the mixture and the solution was stirred for a few minutes then concentrated. The residue was taken up in water and EtOAc. The layers were separated and the EtOAc layer was washed with water until the washes were colorless. The EtOAc layer was then washed with brine, dried over MgSO$_4$, filtered and concentrated to a light tan oil, weight 23.5 g (64%). Dimethyl-2R-methyl-3-p-toluenesulfonyl-3-azapentanoate was prepared in the same manner. $^1$H NMR (CDCl$_3$, 300 MHz) δ 1.35 (d, J=7.2 Hz, 3H), 2.39 (s, 3H), 3.51 (s, 3H), 3.70 (s, 3H), 4.01 (d, J=19 Hz, 1H), 4.26 (d, J=19 Hz, 1H), 4.50 (q, J=7.2, 15 Hz, 1H), 7.27 (d, J=8.1 Hz, 2H), 7.74 (d, J=8.4 Hz, 2H); $^{13}$C NMR (CDCl$_3$, 100 MHz) δ 16.3, 21.5, 45.3, 52.1, 52.2, 54.5, 127.6, 129.4, 136.4, 143.7, 170.2, 171.7; MS (FAB+ DTT:DTE) m/z 330 (M+), 270 (—CO$_2$CH$_3$).

8C. Preparation of 2S-Methyl-3-p-toluenesulfonyl-3-azapentandioic acid

A solution of dimethyl 2S-methyl-3-p-toluenesulfonyl-3-azapentandioate (23.5 g, 71.3 mmol) in Tiff (250 ml) was cooled in an ice-water bath. Aqueous NaOH solution (1N, 200 ml) was gradually added to the solution and the mixture was stirred. The ice bath was removed and the mixture was allowed to warm to room temperature. After 1 hour, the mixture was acidified by addition of 250 ml of 1N HCl and concentrated to ~50 ml volume. The aqueous mixture was extracted with 500 ml of EtOAc. The EtOAc layer was washed with 50 ml of water, brine, dried over MgSO$_4$, filtered and concentrated to give an amber colored oil. CH$_2$Cl$_2$ was added to the residue and evaporated to give an off-white solid, 20.6 g. The solid was recrystallized from EtOAc and hexanes to give 19.1 g of spherical crystals (89%). 2R-Methyl-3-p-toluenesulfonyl-3-azapentandioic acid was prepared in the same manner. $^1$H NMR (DMSO-d$_6$, 300 MHz) δ 1.28 (d, J=7.5 Hz, 3H), 2.36 (s, 3H), 3.96 (d, J=18 Hz, 1H), 4.08 (d, J=18 Hz, 1H), 4.26–4.38 (m, 1H), 7.35 (d, J=8.4 Hz, 2H), 7.71 (d, J=8.4 Hz, 2H), 12.69 (br s, 2H). $^{13}$C NMR (DMSO-d$_6$, 100 MHz) δ 16.2, 21.0, 45.8, 54.5, 127.1, 129.5, 136.7, 143.2, 171.1, 172.2.

8D. Synthesis of Dimethyl 2S ,5R, 10S-trimethyl-4,8-dioxa-6-p-toluenesulfonyl-3,6,9-triazaundecanedioate N,N-Dimethylacetamide (450 ml) was degassed, and R-2-methyl-N-p-toluenesulfonyliminodiacetic acid (14.05 g, 46.3 mmol), S-alanine methyl ester hydrochloride (16.47 g, 118.0 mmol), and hydroxybenzotriazole hydrate (19.05 g, 124.4 mmol) were added. A few minutes later, triethylamine (16.5 ml, 118 mmol) and EDC.HCl (24.54 g, 128 mmol) were added and the mixture was stirred overnight. After 15 h, the solvent was removed under reduced pressure, and the residue was briefly placed under vacuum. Ethyl acetate (250 ml) and water (125 ml) were added, and the mixture was agitated briefly. The layers were separated and the aqueous layer was washed with ethyl acetate (100 ml). The combined organic layers were washed successively with saturated sodium bicarbonate (twice), 1M HCl (twice), and saturated sodium chloride (once). After drying (Na$_2$SO$_4$) and filtration, the solvent was removed under reduced pressure, giving a white solid (21.17 g, 4.99 mmol, 97% yield): $^1$H NMR (CDCl$_3$, 400 MHz) δ 1.27 (d, J=7.0 Hz, 3H), 1.32 (d, J=7.3 Hz, 3H), 1.40 (d, J=7.0 Hz, 3H), 2.38 (s, 3H), 3.65 (s, 3H), 3.69 (s, 3H), 3.80 (d, J=16.9 Hz, 1H), 3.97 (d, J=16.9 Hz, 1H), 4.25 (q, J=7.2 Hz, 1H), 4.33 (quint, J=7.3 Hz, 1H), 4.55 (quint, J=7.3 Hz, 1H), 7.07 (d, J=7.5 Hz, 1H), 7.26 (d, J=8.1 Hz, 2H), 7.78 (d, J=8.3 Hz, 2H), 8.30 (d, J=7.3 Hz, 1H); $^{13}$C NMR (CDCl$_3$, 100 MHz) δ 14.86, 16.95, 18.00, 21.57, 47.51, 48.32, 48.42, 52.26, 52.42, 56.55, 128.06, 129.77, 135.35, 144.41, 169.12, 70.60, 172.97, 173.09.

8E. Preparation of 2S ,5R, 10S-Trimethyl-6-p-toluenesulfonyl-4.8-dioxo-3,6,9-triazaundecanedioic acid Dimethyl 2S,5R, 10S-trimethyl-6-p-toluenesulfonyl-4,8-dioxo-3,6,9-triazaundecandioate (21.17 g, 44.90 mmol) was hydrolyzed using the procedure described in Example 8C in 180 ml of THF and using NaOH (3.59 g, 89.79 mmol) in 90 ml of water. A dry foam was obtained, weight 20.9 g. $^1$H NMR (DMSO-d$_6$, 400 MHz) ≠7 1.06 (d, J=7.0 Hz, 3H), 1.25 (d, J=7.2 Hz, 3H); 1.30 (d, J=7.2 Hz, 3H), 2.40 (s, 3H), 3.75 (d, J=17.5 Hz, 1H), 4.03 (d, J=17.5 Hz, 1H), 3.98–4.11 (m, 1H), 4.25–4.38 (m, 2H), 7.39 (d, J=8.1 Hz, 2H), 7.77 (d, J=8.1 Hz, 2H), 8.48 (d, J=7.5 Hz, 1H), 8.96 (d, J=7.0 Hz, 1H), 12.56 (br s, 2H); $^{13}$C NMR (DMSO-d$_6$, 100 MHz) δ 15.4, 16.9, 17.6, 21.1, 46.8, 47.7, 47.8, 55.5, 127.5, 129.7, 135.7, 143.7, 169.2, 170.8, 173.7.

8F. Preparation of 3S,6R,11S-Trimethyl-2,5,9,12-tetraoxo-7-p-toluenesulfonyl-1,4,7,10,13-pentaazacyclopentadecane.

Ethylene diamine (151 μl, 2.25 mmol) and triethylamine (629 μl, 451 mmol) were added to a solution of 2S,5R,10S-trimethyl-6-p-toluenesulfonyl-4-8-dioxo-3,6,9-triazaundecanedioic acid (1.00 g, 2.25 mmol) in 450 ml of degassed DMF. The solution was cooled to between −40° and −50° C. under argon atmosphere and diphenylphosphoryl azide (1.16 ml, 5.40 mmol) was added. The reaction was stirred and allowed to slowly warm to room temperature overnight. After ~16 h, The reaction mixture was concentrated in vacuo and the residue was dissolved in EtOAc and water. The EtOAc layer was separated, washed with water, aq. NaHCO$_3$, 0.5N KHSO$_4$, water, brine, and dried over MgSO$_4$, filtered, and concentrated to an oil. The oil was dissolved in ~15 ml of CH$_3$CN and filtered. EtOAc and diethyl ether (Et$_2$O) were added to the concentrated solution and fluffy white solid formed to give 200 mg. The solid was purified by column chromatography on silica gel using 5% MeOH in CH$_2$Cl$_2$ as eluent. The product was collected as a white solid, 129 mg (12%). $^1$H NMR (CDCl$_3$, 400 MHz) δ 1.10–1.18 (m, 6H), 1.33 (d, J=7.0 Hz, 3H), 2.38 (s, 3H), 3.17–3.35 (m, 3H), 3.38–3.49 (m, 1H), 3.88–3.96 (m, 1H), 4.17–4.30 (m, 3H), 4.32–4.42 (m, 1H), 6.86 (br s, 1H), 7.11 (br s, 1H), 7.29 (d, J=8.1 Hz, 2H), 7.69 (br s, 1H), 7.76 (d, J=8.1 Hz, 2H), 8.42 (d, J=8.1 Hz, 1H); $^{13}$C NMR (100 MHz, CDCl$_3$) δ 14.1, 16.4, 17.8, 21.5, 37.9, 38.8, 46.8, 49.7, 50.8, 56.7, 127.8, 130.0, 135.3, 144.7, 170.8, 172.6, 172.9; FAB mass spectrum (NBA+Li) m/z 474 [M+Li]$^+$, 480 [M−H+2Li]$^+$, 516 [M+Li+LiCl]$^+$.

Example 9

9A. Preparation of 2R,3R-Cyclohexano-6S, 9R, 14S-trimethyl-5,8,12,15-tetraoxo-10-p-toluenesulfonyl-1,4,7,10,13-pentaazacyclopentadecane.

A 5 L round bottomed flask was charged with 2S,5R,10S-trimethyl-6-p-toluenesulfonyl-4,8-dioxo-3,6,9-triazaundecanedioic acid (6.65 g, 15.00 mmol), prepared as in Example 8E, in 3 L of anhydrous DMF. The clear solution was cooled in an ice-water bath, and HOBT.H$_2$O and EDC.HCl were added. After 15 min, 1R,2R-diaminocyclohexane in ~750 ml of DMF was added to the solution via cannula. The addition was complete after ~30 min. The solution was allowed to slowly warm to room temperature overnight. After 16 h, the reaction mixture was concentrated to 20 ml volume and diluted with EtOAc and aqueous NaHCO$_3$. The layers were separated and the aqueous layer was extracted with EtOAc four times. The EtOAc layers were combined and washed with 0.5N NaHSO$_4$, H$_2$O, and brine, then concentrated. Some precipitate that formed after washing the EtOAc layer with water was rinsed with water, dissolved in MeOH and added to the crude product. The crude product, 7.7 g, was heated in 500 ml of acetonitrile and filtered. The product was collected as a white solid, weight 4.00 g (51%). $^1$H NMR (CDCl$_3$ with 10% CD$_3$OD, 400 MHz) δ 1.00–1.20 (m, 13H), 1.51–1.63 (m, 2H), 1.72–1.90 (m, 2H), 2.28 (s, 3H), 3.33–3.41 (m, 3H), 3.98–4.14 (m, 4H), 7.20 (d, J=8.0 Hz, 2H), 7.63 (d, J=8.4 Hz, 2H); $^{13}$C NMR (CDCl$_3$ with 10% CD$_3$OD, 100 MHz) δ 13.8, 15.6, 17.0, 21.1, 24.3, 24.4, 31.8, 31.9, 45.6, 49.3, 49.6, 52.3, 52.7, 56.8, 127.3, 129.7, 135.3, 144.3, 169.9, 171.3, 171.4, 173.2; FAB mass spectrum (TGL) m/z 522 (M+H).

Example 10
Stopped-Flow Kinetic Analysis

Stopped-flow kinetic analysis has been utilized to determine whether a compound can catalyze the dismutation of superoxide (Riley, D. P., Rivers, W. J. and Weiss, R. H., "Stopped-Flow Kinetic Analysis for Monitoring Superoxide Decay in Aqueous Systems," Anal. Biochem, 196, 344–349 [1991]). For the attainment of consistent and accurate measurements all reagents were biologically clean and metal-free. To achieve this, all buffers (Calbiochem) were biological grade, metal-free buffers and were handled with utensils which had been washed fast with 0.1N HCl, followed by purified water, followed by a rinse in a 10$^{-4}$M EDTA bath at pH 8, followed by a rinse with purified water and dried at 65° C. for several hours. Dry DMSO solutions of potassium superoxide (Aldrich) were prepared under a dry, inert atmosphere of argon in a Vacuum Atmospheres dry glovebox using dried glassware. The DMSO solutions were prepared immediately before every stopped-flow experiment. A mortar and pestle were used to grind the yellow solid potassium superoxide (~100 mg). The powder was then ground with a few drops of DMSO and the slurry transferred to a flask containing an additional 25 ml of DMSO. The resultant slurry was stirred for ½ h and then filtered. This procedure gave reproducibly ~2 mM concentrations of superoxide in DMSO. These solutions were transferred to a glovebag under nitrogen in sealed vials prior to loading the syringe under nitrogen. It should be noted that the DMSO/superoxide solutions are extremely sensitive to water, heat, air, and extraneous metals. A fresh, pure solution has a very slight yellowish tint.

Water for buffer solutions was delivered from an in-house deionized water system to a Barnstead Nanopure Ultrapure Series 550 water system and then double distilled, first from alkaline potassium permanganate and then from a dilute EDTA solution. For example, a solution containing 1.0 g of potassium permanganate, 2 liters of water and additional sodium hydroxide necessary to bring the pH to 9.0 were added to a 2-liter flask fired with a solvent distillation head. This distillation will oxidize any trace of organic compounds in the water. The final distillation was carried out under nitrogen in a 2.5-liter flask containing 1500 ml of water from the first still and 1.0×10$^{-6}$M EDTA. This step will remove remaining trace metals from the ultrapure water. To prevent EDTA mist from volatilizing over the reflux arm to the still head, the 40-cm vertical arm was packed with glass beads and wrapped with insulation. This system produces deoxygenated water that can be measured to have a conductivity of less than 2.0 nanomhos/cm$^2$.

The stopped-flow spectrometer system was designed and manufactured by Kinetic Instruments Inc. (Ann Arbor, MI) and was interfaced to a MAC IICX personal computer. The software for the stopped-flow analysis was provided by Kinetics Instrument Inc. and was written in QuickBasic with MacAdios drivers. Typical injector volumes (0.10 ml of buffer and 0.006 ml of DMSO) were calibrated so that a large excess of water over the DMSO solution were mixed together. The actual ratio was approximately 19/1 so that the initial concentration of superoxide in the aqueous solution was in the range 60–120 μM. Since the published extinction coefficient of superoxide in H$_2$O at 245 nm is ~2250M$^{-1}$ cm$^{-1}$ (1), an initial absorbance value of approximately 0.3–0.5 would be expected for a 2-cm path length cell, and this was observed experimentally. Aqueous solutions to be mixed with the DMSO solution of superoxide were prepared using 80 mM concentrations of the Hepes buffer, pH 8.1 (free acid+Na form). One of the reservoir syringes was filled with 5 ml of the DMSO solution while the other was filled with 5 ml of the aqueous buffer solution. The entire injection block, mixer, and spectrometer cell were immersed in a thermostatted circulating water bath with a temperature of 21.0°±0.5° C.

Prior to initiating data collection for a superoxide decay, a baseline average was obtained by injecting several shots of the buffer and DMSO solutions into the mixing chamber. These shots were averaged and stored as the baseline. The first shots to be collected during a series of runs were with aqueous solutions that did not contain catalyst This assures that each series of trials were free of contamination capable of generating first-order superoxide decay profiles. If the decays observed for several shots of the buffer solution were second-order, solutions of manganese(II) complexes could be utilized. In general, the potential SOD catalyst was screened over a wide range of concentrations. Since the initial concentration of superoxide upon mixing the DMSO with the aqueous buffer was ~$1.2 \times 10^{-4}$M, we wanted to use a manganese (II) complex concentration that was at least 20 times less than the substrate superoxide. Consequently, we generally screened compounds for SOD activity using concentrations ranging from $5 \times 10^{-7}$ to $8 \times 10^{-6}$M. Data acquired from the experiment was imported into a suitable math program (e.g., Cricket Graph) so that standard kinetic data analyses could be performed. The catalytic rate constant for dismutation of superoxide by the manganese(II) complex of Example 1 was determined from the linear plot of observed rate constants ($k_{obs}$) versus the concentration of the manganese(II) complexes. $k_{obs}$ values were obtained from the liner plots of in absorbance at 245 nm versus time for the dismutation of superoxide by the manganese(II) complex. The $k_{cat}$ ($M^{-1}sec^{-1}$) of the manganese (II) complex of Examples 1–3 at pH=8.1 and 21° C. were determined and the results can be found in Table I.

The manganese(II) complexes of fifteen-membered pentaazamacrocyclic ligand in Examples 1–3 are effective catalysts for the dismutation of superoxide, as can be seen from the $k_{cat}$ data in Table I.

TABLE I

| Example No. | $k_{cat}$ ($M^{-1}sec^{-1}$) |
| --- | --- |
| 1 | $3.92 \times 10^7$ |
| 2 | $1.29 \times 10^7$ |
| 3 | $1.36 \times 10^7$ |

What is claimed is:

1. A process for preparing a substituted polyazamacrocycle comprising contacting (a) a diamine represented by the formula:

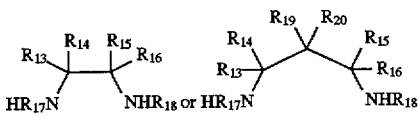

and (b) a dicarboxylic acid or ester thereof represented by the formula:

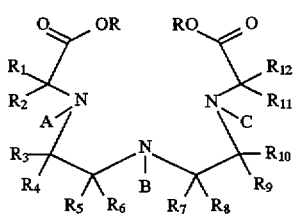

or an anhydride thereof; in the presence of a suitable base and a suitable solvent under reactions conditions sufficient to produce said substituted polyazamacrocycle represented by the formula:

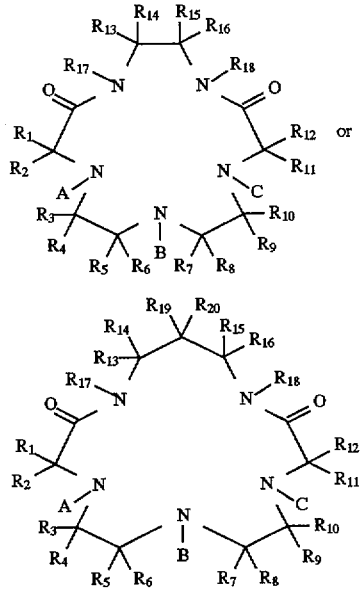

provided that when an ester of said dicarboxylic acid is used, said suitable base is optional, and when said dicarboxylic acid or an anhydride of said dicarboxylic acid is used, the reaction mixture further comprises a suitable coupling agent; wherein $R_1$, $R_2$, $R_3$, $R_4$, $R_5$, $R_6$, $R_7$, $R_8$, $R_9$, $R_{10}$, $R_{11}$ and $R_{12}$ are independently selected from hydrogen or alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals or radicals attached to the α-carbon of α-amino acids; or $R_3$ or $R_4$ and $R_5$ or $R_6$, and $R_7$ or $R_8$ and $R_9$ or $R_{10}$ together with the carbon atoms to which they are attached independently form a sainted, partially saturated or unsaturated cyclic ring structure having 3 to 20 carbon atoms; or $R_1$ or R2 and $R_3$ or $R_4$, $R_5$ or $R_6$ and $R_7$ or $R_8$, and $R_9$ or $R_{10}$ and $R_{11}$ or $R_{12}$ together with the carbon atoms to which they are attached independently form a nitrogen containing heterocycle having 2 to 20 carbon atoms provided that when the nitrogen containing heterocycle is an aromatic heterocycle which does not contain a substituent attached to the nitrogen, the hydrogen attached to the nitrogen in said formula, which nitrogen is also in the macrocycle and the R groups attached to the same carbon atoms of the macrocycle are absent;

$R_1$ and $R_2$, $R_3$ and $R_4$, $R_5$ and $R_6$, $R_7$ and $R_8$, $R_9$ and $R_{10}$, and $R_{11}$ and R12 together with the carbon atom to which they are attached independently form a saturated, partially saturated or unsaturated ring structure having 3 to 20 carbon atoms, or $R_1$ and $R_2$, $R_3$ and $R_4$, $R_5$ and $R_6$, $R_7$ and $R_8$, $R_9$ and $R_{10}$, and $R_{11}$ and $R_{12}$ independently are ═O or ═S; and combinations thereof; and wherein $R_{13}$, $R_{14}$, $R_{15}$, $R_{16}$, $R_{19}$ and $R_{20}$ are independently selected from hydrogen or alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals; or $R_{13}$ and $R_{14}$, $R_{15}$ and $R_{16}$, and $R_{19}$ and $R_{20}$ together with the carbon atom to which they are attached independently form a saturated, partially saturated or unsaturated ring structure having 3 to 20 carbon atoms; or $R_{19}$ and $R_{20}$ are independently —$OR_{23}$, —OH, —$SR_{23}$, —$NR_{23}R_{24}$, —P(O)($OR_{25}$)($OR_{26}$) or —P(O)($R_{25}$)($OR_{26}$); or $R_{19}$ and $R_{20}$ are =O, =S, =$NR_{23}$, =N—OH, =N—$OR_{23}$, =N—O—C(O)—$R_{23}$, or =$CR_{23}R_{24}$; or $R_{13}$ or $R_{14}$ and $R_{15}$ or $R_{16}$ together with the carbon atoms to which they are attached independently form a saturated, partially saturated or unsaturated cyclic having 3 to 20 carbon atoms, provided that if said dime has three carbons between the nitrogen atoms, the saturated, partially saturated or unsaturated cyclic has 4 to 20 carbon atoms; or $R_{13}$ or $R_{14}$ and $R_{19}$ or $R_{20}$, or $R_{15}$ or $R_{16}$ and $R_{19}$ or $R_{20}$ together with the carbon atoms to which they are attached independently form a saturated, partially saturated or unsaturated cyclic ring structure having 3 to 20 carbon atoms; and combinations thereof;

wherein $R_{17}$ and $R_{18}$ are independently selected from hydrogen and alkyl or aryl groups;

wherein R is hydrogen or alkyl or aryl groups;

wherein $R_{23}$ and $R_{24}$ are independently selected from alkyl, aralkyl or aryl groups;

$R_{25}$ and $R_{26}$ are independently selected from hydrogen, alkyl, aralkyl or aryl groups and wherein A, B and C are independently selected from hydrogen, alkyl, aryl, aralkyl, cycloalkyl, —$OR_{21}$, —$SO_2R_{21}$, —$COOR_{21}$, —$COR_{21}$, —$CONR_{21}R_{22}$, $R_{21}R_{22}$P(O), ($R_{21}$O)($R_{22}$O)P(O), $R_{21}R_{22}$P(S), —$SOR_{21}$ or —Si($OR_{21}$)$_3$, provided that when the two "R" groups on a carbon adjacent to the nitrogen are =O or =S , A, B and C are hydrogen, alkyl, aralkyl or aryl and $R_{21}$ and $R_{22}$ are independently selected from hydrogen, alkyl, aryl, aralkyl or alkaryl groups.

2. The process of claim 1 wherein said coupling agent is selected from the group consisting of phosphoryl azides, carbodiimides, cyanamides, ketenimines, isoxazolium salts, monocyclic nitrogen containing heterocyclic amides of aromatic character containing 1 to 4 nitrogens in the ring, alkoxylated acetylene, reagents which form a mixed anhydride with the carboxyl moiety of the dicarboxylic acid, nitrogen coming heterocyclic compounds having a hydroxy group on one ring nitrogen or carbonates thereof in conjunction with a coupling agent from one of the other groups, reagents which form an active ester with the carboxyl moiety of the dicarboxylic add, benzotriazol-1-yloxy-tris(dimethylamino)phosphonium hexafluorophosphate, re-dox based coupling agents, and mixtures thereof.

3. The process of claim 2 wherein said coupling agent is diphenylphosphoryl azide or 1-(3-dimethylaminopropyl)-3-ethylcarbodiimide hydrochloride and hydroxybenzotriazole.

4. The process of claim 1 wherein said solvent is a polar organic solvent.

5. The process of claim 1 wherein said base is selected from the group consisting of trialkylamines, pyridines and imidazoles.

6. The process of claim 1 wherein R is hydrogen.

7. The process of claim 1 wherein said dime is represented by the formula:

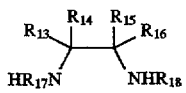

8. The process of claim 7 wherein $R_3$, $R_{14}$, $R_5$ and $R_{16}$ are independently selected from hydrogen or alkyl; or $R_{13}$ or $R_{14}$ and $R_{15}$ or $R_{16}$ together with the carbon atoms to which they are attached independently form a saturated, partially saturated or unsaturated cyclic having 3 to 20 carbon atoms.

9. The process of claim 8 wherein at least one of $R_{13}$, $R_{14}$, $R_{15}$ and $R_{16}$ is an alkyl group.

10. The process of claim 9 wherein at least one of $R_{13}$ and $R_{14}$ and at least one of $R_{15}$ and $R_{16}$ is an alkyl group.

11. The process of claim 8 wherein $R_{13}$ and $R_{16}$ together with the carbon atoms to which they are attached independently form a saturated, partially saturated or unsaturated cyclic ring structure having 3 to 20 carbon atoms and $R_{14}$ and $R_{15}$ are hydrogen.

12. The process of claim 1 wherein said diamine is represented by the formula:

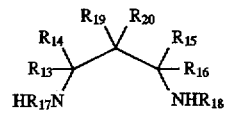

13. The process of claim 12 wherein $R_{13}$, $R_{14}$, $R_{15}$, $R_{16}$, $R_{19}$ and $R_{20}$ are independently selected from hydrogen or alkyl; or $R_{13}$ or $R_{14}$ and $R_{19}$ or $R_{20}$, or $R_{15}$ or $R_{16}$ and $R_{19}$ or $R_{20}$ together with the carbon atoms to which they are attached independently form a saturated, partially saturated or unsaturated cyclic ring structure having 3 to 20 carbon atoms; or $R_{19}$ and $R_{20}$ together are =O or =S.

14. The process of claim 1 wherein $R_1$, $R_2$, $R_3$, $R_4$, $R_5$, $R_6$, $R_7$, $R_8$, $R_9$, $R_{10}$, $R_{11}$ and $R_{12}$ are independently selected from hydrogen, alkyl radicals or radicals attached to the α-carbon of α-amino acids; or $R_3$ or $R_4$ and $R_5$ or $R_6$, and $R_7$ or $R_8$ and $R_9$ or $R_{10}$ together with the carbon atoms to which they are attached independently form a saturated, partially saturated or unsaturated cyclic ring structure having 3 to 20 carbon atoms; or $R_1$ and $R_2$, $R_3$ and $R_4$, $R_5$ and $R_6$, $R_7$ and $R_8$, $R_9$ and $R_{10}$, and $R_{11}$ and $R_{12}$ independently are =O or =S .

15. The process of claim 14 wherein at least one of $R_3$ or $R_4$ and $R_5$ or $R_6$, and $R_7$ or $R_8$ and $R_9$ or $R_{10}$ together with the carbon atoms to which they are attached independently form a saturated, partially saturated or unsaturated cyclic having 3 to 20 carbon atoms, and the remaining of $R_1$, $R_2$, $R_3$, $R_4$, $R_5$, $R_6$, $R_7$, $R_8$, $R_9$, $R_{10}$, $R_{11}$ and $R_{12}$ are independently selected from hydrogen, alkyl radicals or radicals attached to the α-carbon of α-amino acids.

16. The process of claim 14 wherein at least one of $R_1$, $R_2$, $R_3$, $R_4$, $R_5$, $R_6$, $R_7$, $R_8$, $R_9$, $R_{10}$, $R_{11}$ and $R_{12}$ are alkyl radicals or radicals attached to the α-carbon of α-amino acids, and the remaining of $R_1$, $R_2$, $R_3$, $R_4$, $R_5$, $R_6$, $R_7$, $R_8$, $R_9$, $R_{10}$, $R_{11}$ and $R_{12}$ are hydrogen.

17. The process of claim 14 wherein R is hydrogen.

18. The process of claim 17 wherein A, B and C are independently selected from the group consisting of hydrogen, alkyl, aryl and aralkyl.

19. The process of claim 1 wherein $R_{17}$ and $R_{18}$ are hydrogen.

20. The process of claim 1 further comprising reducing said substituted polyazamacrocycle to produce a reduced substituted polyazamacrocycle of the formula:

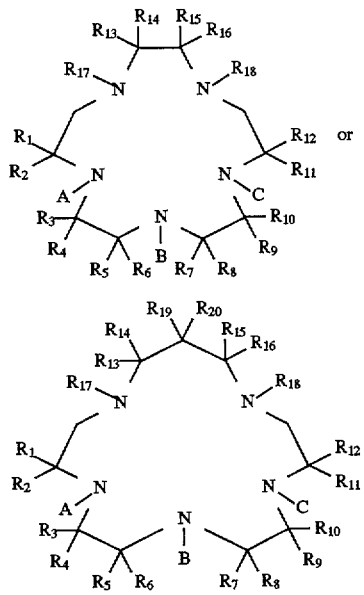

wherein A, B and C are independently selected from hydrogen, alkyl, aryl, aralkyl and cycloalkyl groups.

21. The process of claim 20 wherein said reduction is conducted in the presence of a reducing agent selected from the group consisting of aluminum hydrides and boron hydrides.

22. The process of claim 21 wherein said reducing agent is selected from the group consisting of lithium aluminum hydride, borane and sodium bis(2-methoxyethoxy) aluminum hydride.

23. The process of claim 20 further comprising reacting said reduced substituted polyazamacrocycle with a manganese compound under essentially anhydrous and anaerobic conditions to produce a manganese complex represented by the formula:

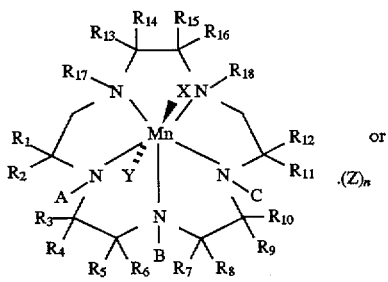

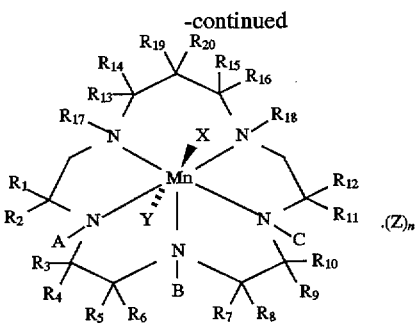

and, optionally, further conducting an exchange reaction with said manganese complex to exchange the ligands X, Y and Z on said manganese complex; wherein X, Y and Z are ligands independently selected from the group consisting of halide, oxo, water, hydroxy, alcohol, phenol, dioxygen,, peroxy, hydroperoxo, alkylperoxo, arylperoxo, ammonia, alkylamino, arylamino, hetcrocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic add, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetralkyl borate, tartrate, salicylate, succinate, citrate, ascorbate, saccharinate, amino acid, hydroxamic acid, thiotosylate, and anions of ion exchange resins, or the corresponding anion s thereof, or X, Y and Z are independently attached to one or more of the "R" groups and n is an integer from 0 to 3.

24. The process of claim 23 wherein X, Y acid Z are independently selected form the group consisting of halide, organic acid, nitrate and bicarbonate anions.

* * * * *